United States Patent [19]

Hosmane et al.

[11] Patent Number: 5,843,912
[45] Date of Patent: Dec. 1, 1998

[54] RING-EXPANDED NUCLEOSIDES AND NUCLEOTIDES

[75] Inventors: Ramachandra Hosmane, Columbia; Barry Burns, Owings Mills, both of Md.

[73] Assignees: Universy of Maryland, Baltimore, Md.; Nabi, Boca Raton, Fla.

[21] Appl. No.: 518,278

[22] Filed: Aug. 23, 1995

Related U.S. Application Data

[63] Continuation-in-part of Ser. No. 268,570, Jul. 6, 1994, abandoned.
[51] Int. Cl.$^6$ .......................... A61K 31/70; A07H 19/04; A01N 43/36; A01N 43/713
[52] U.S. Cl. .............................. 514/43; 514/81; 514/393; 514/421; 536/27.13
[58] Field of Search ........................... 536/27.13; 514/43, 514/81, 393, 421

[56] References Cited

PUBLICATIONS

Wang et al. Nucleosides & Nucleotides 13(10): 2307–2320 (1994).

*Primary Examiner*—Gary L. Kunz
*Attorney, Agent, or Firm*—Cushman, Darby & Cushman, IP Group of Pillsbury, Madison & Sutro LLP

[57] ABSTRACT

The present invention relates to compositions comprising analogues of purine nucleosides containing a ring-expanded ("fat") heterocyclic ring, in place of purine, and an unmodified or modified sugar residue, pharmaceutically acceptable derivatives of such compositions, as well as methods of use thereof. In particular, these compositions may be utilized in the treatment of certain cancers, bacterial, fungal, parasitic, and viral infections, including, but not limited to, Acquired Immunodeficiency Syndrome (AIDS) and hepatitis.

16 Claims, 5 Drawing Sheets

COFORMYCIN

2'-DEOXYCORMYCIN
(PENTOSTATIN)

AZEPINOMYCIN

RING-EXPANDED NUCLEOSIDES AND NUCLEOTIDES

This application is a continuation-in-part of Ser. No. 08/268,570 filed Jul. 6, 1994, now abandoned.

BACKGROUND OF THE INVENTION

Technical Field

The present invention relates to compositions comprising analogues of purine nucleosides containing a ring-expanded ("fat" or "REN", used interchangeably) heterocyclic ring, in place of purine, and an unmodified or modified sugar residue, pharmaceutically acceptable derivatives of such compositions, as well as methods of use thereof. In particular, these compositions can be utilized in the treatment of certain cancers, bacterial, fungal, parasitic, and viral infections, including, but not limited to, Acquired Immunodeficiency Syndrome (AIDS) and hepatitis.

The concept of the present invention can be extended to include pyrimidine nucleosides and pharmaceutically acceptable derivatives thereof.

Background Information

Acquired Immunodeficiency Syndrome (AIDS) has become the deadliest epidemic of the closing years of the 20th century (Benditt, J., Ed., "AIDS, The Unanswered Questions," *Science* 260:1253–93 (1993); Mitsuya, et al., *Science* 249:1533–44 (1990); Fauci, *Proc. Natl. Acad. Sci. USA* 83:9278 (1986); *Chemical and Engineering News* Jan. 19, 1987, p. 30, Jan. 26, 1987, p. 18, Jun. 8, 1987, p. 6, Jun. 29, 1987, p. 25; Nov. 23, 1989, pp. 12–70; Jun. 26, 1989, pp. 7–16; and Jul. 5, 1993, pp.20–27). It is caused by a retrovirus called the human immunodeficiency virus (HIV). Retroviruses contain ribonucleic acid (RNA) in their genomes instead of deoxyribonucleic acid (DNA) as is the case with mammals, including humans, and many other bacteria and viruses.

When the virus infects host cells, it uses its own enzyme called reverse transcriptase to transcribe its RNA blue-print into a double-stranded DNA, using the host nucleotide pool. The newly synthesized viral DNA, known as provirus, then gets incorporated into host cellular DNA. The host genetic machinery is then utilized to crank out new viral particles which further infect other cells, and so on.

Several approaches are currently being undertaken to confront the virus, for example, immunological reconstitution, development of a vaccine, and antiretroviral therapy. This third approach is described herein.

While the most desirable approach to check the AIDS viral epidemic would be the development of a vaccine, there are compelling factors to suggest that this approach alone will not be adequate to halt the epidemic. These factors are: (a) unlike other retroviruses, by infecting T4-lymphocytes, the HIV eliminates the very component of the immune response that recognizes antigens, and (b) the virus undergoes continually rapid mutation, resulting in several variations of viral envelope proteins, and hence viral antigenicity. This is believed to be due to high error rates intrinsic to reverse transcriptase-catalyzed genome replication (i.e., 10 times as compared with that catalyzed by human DNA polymerases) (Presson, et al., *Science* 242:1168 (1988); Roberts, et al., *Science* 242:1171 (1988)). Therefore, simply restoring an AIDS patient's immune system, without eliminating or at least checking the extent of HIV infection, is unlikely to prove effective therapeutically. Thus, with the unlikelihood that the exponential growth and spread of the disease will be halted in the very near future by vaccine development, it is of the utmost importance to pursue antiretroviral therapy.

An antiretroviral therapeutic approach involves developing agents that can potentially suppress the replication of human immunodeficiency virus (HIV) by any of a number of mechanisms including, but not limited to, the following: (a) blocking the viral attachment to the target cell, (b) inhibiting the enzyme reverse transcriptase, and/or (c) blocking transcription and/or translation. While progress is being made on several fronts, the principal obstacle has been the non-specificity and/or toxicity of many otherwise promising antiviral agents. In this respect, exploitation of the intrinsically high error rate; Presson, et al., *Science* 242:1168 (1988); Roberts, et al., *Science* 242:1171 (1988), of HIV reverse transcriptase to incorporate a chain-terminating nucleotide residue into the developing DNA (approach c) has good prospects for specificity.

As mentioned above, HIV reverse transcriptase makes; 10 times as many errors as compared to other cellular polymerases (Presson, et al., *Science* 242:1168 (1988); Roberts, et al., *Science* 242:1171 (1988)). Thus, the incorporation of the chain-terminating nucleotide residue has the potential advantage of specificity in that it is less likely that the normal cellular DNA polymerases would easily accept an aberrant nucleotide analogue. In fact, AZT (Mitsuya, et al., *Proc. Natl. Acad. Sci. USA* 82:7096 (1985)) (3'-azido-3'-deoxythymidine), DDI (2',3'-dideoxyinosine) (Mitsuya et al., *Nature* 353:269 (1991)) and DDC (2',3'-dideoxycytidine) (Nasr et al., *Antiviral Res.* 14:125 (1990); Merigan et al., *Am. J. Med.* 88:11 (1990); Meng et al., *Ann. Intern. Med.* 116:13 (1992)), the currently approved therapy for AIDS, are known to operate by this chain termination mechanism. The other prospective drugs, for example, DDA and CS-87, are also known to be chain-terminators (Johnston et al., *Science* 260:1286–93 (1993); Mitsuya et al., *Science* 249:1533–44 (1990); *Chemical and Engineering News* Jan. 19, 1987, p. 30, Jan. 26, 1987, p. 18, Jun. 8, 1987, p. 6, Jun. 29, 1987, p. 25; Nov. 23, 1989, pp. 12–70, Jun. 26, 1989, pp. 7–16, and Jul. 5, 1993, pp. 20–27). Unfortunately, they all suffer from either unacceptable levels of toxicity or in vivo non-efficacy, e.g. AZT is toxic to bone marrow, DDC causes painful feet, and DDA & CS-87 are not adequately efficacious in vivo (Johnston et al., supra (1993); Mitsuya et al., supra (1990); *Chemical and Engineering News* Jan. 19, 1987, p. 30, Jan. 26, 1987, p. 18, Jun. 8, 1987, p. 6, Jun. 29, 1987, p. 25; Nov. 23, 1889, pp. 12–70; Jun. 26, 1989, pp. 7–16, and Jul. 5, 1993, pp. 20–27). Therefore, the search must continue for efficient chain-terminators with minimum toxicity so as to arrive at an ideal anti-AIDS drug.

Chain termination can occur by different mechanisms: AZT and the other drugs mentioned above, for example, lack the crucial 3'-OH function necessary for chain elongation. It is also possible that base-mispairing accompanied by considerable deviation of base-ribose conformation from the natural array leads to chain termination (see FIG. I) (Chidgeavadze, et al., *FEBS LETT*, 183:275 (1985); Chidgeavadze, et al., *Biochim. Biophys. Acta*, 868:145 (1986); Beabealashvilli et al., *Biochim. Biophys. Acta*, 868:136 (1986)).

Significant deviation of the 3'—OH group from the natural array would hinder incorporation of subsequent nucleotides into the growing polynucleotide chain and/or formation of the RNA-DNA hybrid, an important event occurring during reverse transcription. The potentially planar and aromatic nucleosides/nucleotides, which are described herein are thought to operate by this latter mechanism, as corroborated by molecular modeling studies. (Huckel MO calculations on potential aromaticity of several heterocyclic aglycons were performed using the program "HMO", available from Trinity Software, Campton, N.H.) Molecular modeling studies were performed on a Silicon Graphics™ computer, employing CHARMm™, interfaced with QUANTA™, obtained from Molecular Simulations, Inc., Boston, Mass. However, several other possible mechanisms of action cannot be ruled out.

FIG. II (A) depicts a ten-nucleotide long oligomer containing all 10 natural nucleotides, FIG. II (B) shows the corresponding oligomer with 9 natural nucleotides plus a "fat" guanine (fG) nucleotide inserted at position 5 in place of G. FIG. II (C) is a space-filling model of FIG. II (B). Extensive ABNR (Adopted Basis Newton Raphson) energy minimization performed on each duplex, Molecular modeling studies were performed on a Silicon Graphics™ computer, employing CHARMm™, interfaced with QUANTA™, obtained from Molecular Simulations, Inc., Boston, Mass., that was formed by hybridization of each oligomer with its respective complementary oligomer, shows that incorporation of a fG into a nucleic acid sequence results in considerable distortion of the double helix with severe disruption of base-pair hydrogen bonding leading to unwinding of the double helix starting from the deviant fG residue (see FIGS. II (B) and II (C)).

Implications are that the incorporation of an fG into the growing DNA chain during reverse transcription would (a) hinder incorporation of subsequent nucleotides, (b) cause base-pair disruption, mismatch, or frameshift, and/or (c) prevent formation of an RNA-DNA hybrid. Any or all of the above events lead to chain termination, and in turn, inhibit viral replication.

Even if an analogue is not a chain-terminator, the incorporation of such an aberrant nucleotide into DNA by HIV reverse transcriptase, could become self destructive, as the analogue may introduce multiple mutations in subsequent rounds of polymerization and accumulations of several such mutations would be lethal to the virus.

Still another possible mode of action that cannot be ignored is if any of the ring-expanded nucleosides turn out to be neither chain terminators nor to be incorporated into DNA. In that case, the inhibitory activity of the analogue may simply be due to its binding to one of the active or allosteric binding sites of HIV reverse transcriptase causing competitive, noncompetitive, or uncompetitive inhibition.

One other major pathogen causing severe consequences is the hepatitis B virus (HBV) which is largely prevalent in third-world countries. It is believed that 80% of the world's liver cancer is caused by HBV. The U.S. currently has 1 million infectious carriers, and chronically active hepatitis will develop in over 25% of carriers and often progresses to cirrhosis. It is estimated that about 5000 people die from cirrhosis each year in the U.S. and about 1000 people die from liver cancer caused by HBV.

Hepatitis B virus is a DNA (2'-deoxyribonucleic acid) virus that infects humans. It is a member of the family of viruses, collectively called hepadnaviruses. These closely related viruses selectively infect either mammalian or avian hosts. Mechanistic studies on the replication of these viruses have explored the important role of reverse transcription of an RNA intermediate, strongly suggesting the viability of reverse transcriptase as a logical therapeutic target.

A few patents exist relating to 5:7—fused heterocycles and nucleosides. The compounds described therein have structural features similar to coformycin and pentostatin, the compounds depicted in FIGS. 3A, 3B and 3C.

In particular, U.S. Pat. No. 4,151,347 describes both coformycin and pentostatin.

U.S. Pat. No. 4,163,839 describes a coformycin analogue referred to as isocoformycin.

U.S. Pat. No. 4,713,372 describes a pentostatin analogue referred to as 2'-chloropentosatin.

U.S. Pat. No. 4,935,505 relates to coformycin analogues such as, for example, azolo diazepine.

The compounds described in the above-referenced U.S. patents are quite distant from those encompassed by the present invention.

SUMMARY OF THE INVENTION

The first aspect of the present invention relates to potentially planar and aromatic, ring-expanded analogues of purine, their nucleoside, nucleotide, and any other pharmaceutically acceptable derivatives thereof, bearing the general formula I, as shown below.

The second aspect of the present invention relates to non-planar non-aromatic ring-expanded analogues of purine heterocyclic bases, their nucleoside, nucleotide, and any other pharmaceutically acceptable derivatives thereof, bearing the general formulas II, III, and IV as shown below.

It should also be pointed out that because of their structural similarity to natural purines, ring-expanded nucleosides or nucleotides are an abundant source of substrates and/or inhibitors of enzymes of purine metabolism, as well as of those requiring ATP or GTP cofactors. Indeed, there is a precedence for their potential ability to inhibit enzymes of purine metabolism. The naturally occurring synergistic antitumor antibiotics, coformycin (Ohno et al., *J. Am. Chem. Soc.* 96:4326 (1974), Umezawa et al., Ger. Offen 2,453,649 (1975), Glazer, *Rev. Drug. Metab. Drug. Interact.* 105:3 (1980); Hawkins, et al., *Nucleosides and Nucleotides* 2:479 (1983)), and 2'-deoxycoformycin (pentostatin) (Woo et al., *J. Heterocycl. Chem.* 11:641 (1974), Baker et al., *J. Am. Chem. Soc.* 101:6127 (1079), Chan, et al., *J. Org. Chem.* 47:3457 (1982), Hanvey, et al., *Biochemistry* 23:904 (1984)), (see FIGS. 3A, 3B and 3C), are 5:7-fused nucleosides containing the imidazo [4,5-d][1,3] diazepine nucleus, and are the two strongest inhibitors of adenosine deaminase (ADA) known, with a $K_i$ as high as $10^{-11}$. Another recently isolated natural product called azepinomycin, also a 5:7-fused system, but a non-nucleoside (see FIGS. 3A, 3B and 3C) containing the imidazo [4,5-e][1,4] diazepine ring, is reported to be an inhibitor of guanase (Umezawa, et al., *Jpn. Kokai Tokyo Koho JP* 58,159,494 [83,159,494]; *Chem. Abstr.* 100:137362x (1984); Isshiki, et al., *J. Antibiot.* 40:1461 (1987); Fujii, et al., *Heterocycles* 27:1163 (1988)). All three molecules and their synthetic analogues however, are non-planar or puckered (Acevedo, et al. *Tetrahedron Lett.* 24:4789 (1983), Acevedo et al., *J. Heterocycl. Chem.* 22:349 (1985), Acevedo, et al., *J. Org. Chem.* 51:1050 (1986)). They also possess tetrahedral geometry at the hydroxyl junction of their seven-membered ring, and therefore, are viewed as transition state analogue inhibitors of ADA (Agarwal et al. "Coformycin and Deoxycoformycin: Tight-binding Inhibitors of Adenosine Deaminase", in "Chemistry and Biology of Nucleosides and Nucleotides," Harmon et al., Academic Press, New York, pp. 159–197 (1978)), or guanase (Umezawa, et al., *Jpn. Kokai Tokyo Koho JP* 58,159,494 83,159,494; *Chem. Abstr.* 100:137362x (1984); Isshiki, et al., *J. Antibiot.* 40:1461 (1987); Fujii, et al., *Heterocycles* 27:1163 (1988)).

The physiological significance of inhibiting ADA lies in the fact that the enzyme inactivates the otherwise potential antiviral and antitumor drugs such as 8-azaadenosine, ara-A or formycin by rapid hydrolysis to the corresponding inosine analogues. While the physiological significance of inhibiting guanase is less clear, several reports have recently appeared regarding detection of abnormally high levels of serum guanase activity in patients with liver disease like hepatitis (Shiota et al., *Jpn. J. Med.* 28:22 (1989), Ito et al., *Hepatology* 8:383 (1988)). High serum guanase activity has also been reported to be a biochemical indicator of rejection in liver transplant recipients (Crary et al., *Transplant Proc.* 21:2315 (1989)).

It should also be noted that, in addition to viruses, bacteria represent a medical therapeutic problem and experience has indicated that, over time, certain strains develop resistance to the commonly used antibacterial agents. It is now known that certain of the purine or pyrimidine nucleoside analogues are useful as antibacterial agents, particularly gram negative bacterial infections.

The compounds of the present invention can be used in the treatment or prophylaxis of bacterial infections. The compounds can also be utilized in the production of medications for the treatment or prophylaxis of bacterial infections. Particular bacteria against which the compounds of the invention are useful include *Escherichia coli, Salmonella spp., Shigella flexneri, Citrobacter freundii, Klebsiella pneumoniae, Vibrio spp., Haemophilus influenzae, Yersinia enterolitica, Pasturella haemolytica,* and *Proteus spp*. These agents are responsible for the following diseases: travelers' diarrhea, urinary tract infections, typhoid fever, cholera, shigellosis, and veterinary diseases including enteritis, and colisepticaemia.

Furthermore, it is known that nucleoside analogues operate synergistically with a wide range of other therapeutic agents, enhancing the therapeutic effects of each in a non-additive manner, raising the therapeutic index, and reducing the risk of toxicities from either compound. The activity of the compounds of the present invention, against a wide range of viral and bacterial infections, as well as their novel mechanism of action, may therefore be particularly useful in combination therapies including various combinations of the present compounds with each other and with other therapeutic and/or synergistic compounds and pharmaceutically acceptable carriers. Such combinations have oral, topical, opthalmic, otic, nasal, intraperitoneal, subcutaneous, intervenous and suppository use. Furthermore, veterinary medical applications are also possible as well as use as a feed additive for vertebrate animals.

Typically, there is an optimum ratio of the compound(s) of the present invention with each other and/or with other therapeutic or potentiating agents (such as transport inhibitors, metabolic inhibitors, renal excretion or glucuronidation inhibitors such as probenecid, acetaminophen, aspirin, lorazepam, cimetidine, ranitidine, clofibrate, indomethacin, ketoprofen, naproxen, etc.) wherein the active agents are present in an optimum ratio. An "optimum ratio" is defined as the ratio of the compound(s) of the present invention with another therapeutic agent or agents such that the overall therapeutic effect is greater than the sum of the effects of the individual therapeutic agents. The optimum ratio is usually observed when the agents are present in ratios of 10:1 to 1:10, 20:1 to 1:20, 100:1 to 1:100, and 500:1 to 1:500. Occassionally, even a vanishingly small amount of one therapeutic agent will suffice to potentiate the activity of one or more other agents. In addition, the use of the compounds of the present invention in combinations is particularly useful in reducing the chance of the development of resistance.

In the antibacterial field, it has previously been found that a wide range of antibiotics is effective in potentiating the activity of nucleoside analogues. This includes agents such as benzylpyrimidines, pyrimidines, sulphonamides, rifampicin, tobramycin, fusidic acid, clindamycin, chloramphenicol, and erythromycin. Therefore, an additional embodiment of the present invention relates to a combination wherein the second agent is at least one of the above-mentioned antiviral or antibacterial agents or classes of agent. It should also be noted that the compounds and combinations of the invention can also be used in conjunction with immune modulating therapeutics and therapy.

In view of the above, the compounds of the present invention provide for a therapeutic combination of these compounds, or a pharmaceutically acceptable derivative thereof. At least one additional therapeutic agent may also be included. Furthermore, one compound of the present invention may also be combined with at least one known and commonly used therapeutic agent. Such grouping of compounds or agents will hereinafter be referred to as "combinations." The combinations may be administered together, for example, in a unitary pharmaceutical formulation, or separately, for example, as combinations of tablets, injections, or other medicaments administered at the same time or at different times with the goal of achieving the desired therapeutic effect.

A "pharmaceutically acceptable" derivative means any pharmaceutically acceptable salt, phosphonate, ester, or salt of such ester, or any other compound which is capable of providing the parent compound or compounds of the present invention or a therapeutically effective metabolite or residue thereof. Examples of pharmaceutically acceptable salts of the present invention and pharmaceutically acceptable derivatives thereof include phosphorus compounds and phosphonates, base salts, e.g., derived from an appropriate base such as an alkali metal, an alkaline earth metal, ammonium and mineral acid salts, such as the hydrochloride.

In view of the above, the present invention encompasses potentially planar, aromatic, ring-expanded ("fat") heterocyclic bases, nucleosides and nucleotide compounds having the structure

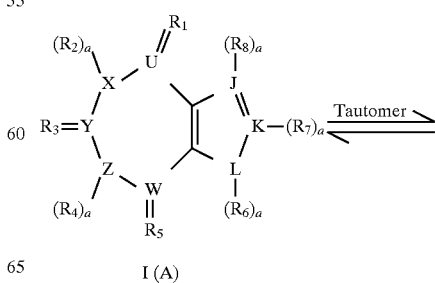

I (A)

-continued

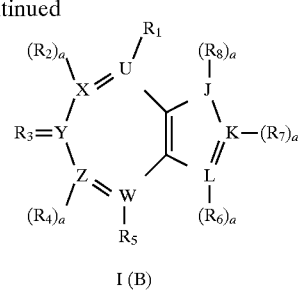

I (B)

Tautomer ↕

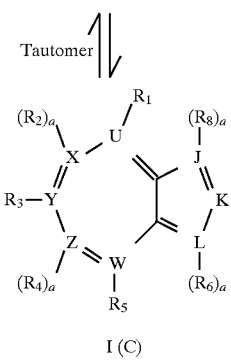

I (C)

wherein:

$R_1$, $R_3$ and $R_5$ are each independently selected from:

NH, $NH_2$, O, OH, S, and SH;

NH-alkyl, N-alkyl, O-alkyl and S-alkyl wherein the alkyl group is $C_1$–$C_{20}$;

NH-aryl, O-aryl and S-aryl wherein the aryl group is a substituted or unsubstituted phenyl or heterocyclic group;

N-glycosyl and NH-glycosyl wherein the glycosyl group is selected from the group consisting of ribosyl, 2'-deoxyribosyl, 2',3'-dideoxyribosyl, 2',3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di- and triphosphate derivatives thereof;

N—$(CH_2)_m$—XR'—$(CH_2)_n$—YR', NH—$(CH_2)_m$—XR'—$(CH_2)_n$—YR', O—$(CH_2)_m$—XR'—$(CH_2)_n$—YR' and S—$(CH_2)_m$—XR'—$(CH_2)_n$—YR' wherein R' is selected from the group consisting of hydrogen, a $C_1$–$C_{20}$ alkyl group, $H_2PO_3$, $H_3P_2O_6$, $H_4P_3O_9$ and the alkali metal or alkaline earth metal salts thereof;

$R_2$, $R_4$, $R_6$, $R_7$, $R_8$ are each independently selected from:

hydrogen, a $C_1$–$C_{20}$ alkyl group, an aryl group which is a substituted or unsubstituted phenyl or heterocyclic group, and an aralkyl group wherein the aryl and alkyl portions of the group have the definitions given above;

a glycosyl group wherein said glycosyl group is selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-difluororibosyl 2',3'-dideoxy-3'-azidoribosyl and mono-, di-, and triphosphate derivatives thereof;

$(CH_2)_m$—XR'—$(CH_2)_n$—YR' wherein R' is selected from the group consisting of:

hydrogen, $H_2PO_3$, $H_3P_2O_6$, $H_4P_3O_9$, and alkali metal or alkaline earth metal salts thereof;

m is zero to 20, n is zero to 20, and a is zero or one; and

U, X, Y, Z, W, J, K, and L are selected from the group consisting of C, N, O, P, and S. U, X, Y, Z, W, J, K and L are selected from the group consisting of carbon (C) and nitrogen.

Formula I(B) can be 4,8-diamino-6-imino-1H-imidazo[4,5-e][1,3]diazepine wherein R, and $R_5$ are $NH_2$, $R_3$ is NH, $R_7$ and $R_8$ are H, and a for $R_2$, $R_4$ and $R_6$ is zero.

Formula I(B) can also be 4,8-diamino-1-benzyl-6-iminoimidazo[4,5-e][1,3]diazepine, wherein $R_1$ and $R_5$ are $NH_2$, $R_3$ is NH, $R_7$ is H, $R_8$ is benzyl ($CH_2Ph$) and a for $R_2$, $R_4$ and $R_6$ is zero.

Formula I(A) can be 6-imino-1H-imidazo[4,5-e][1,3]diazepine-4,8-dione, wherein $R_1$ and $R_5$ are O, $R_3$ is NH; $R_2$, $R_4$, $R_6$ and $R_7$ are H, and a is zero for $R_8$.

Furthermore, formula I(A) can also be 4,6,8-triimino-1-β-D-ribofuranosylimidazo[4,5-e][1,3]diazepine, wherein $R_1$, $R_3$ and $R_5$ are NH, $R_2$, $R_4$ and $R_7$ are H, $R_6$ is 1-β-D-ribofuranosyl, and a for $R_8$ is zero.

Furthermore, it must be noted that the present invention includes all chiral forms and stereoisomers of the compounds presented above.

As noted above, the present invention also includes compounds comprising non-planar, non-aromatic, ring-expanded ("fat") heterocyclic bases, nucleosides or nucleotides having the formula II

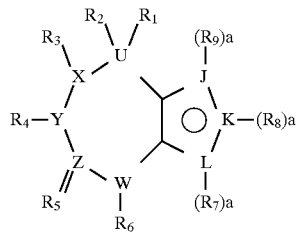

wherein:

$R_1$ and $R_2$ are each independently selected from H, $OR_3$, $SR_3$, $NHR_3$, $CO_2R_3$, $CONHR_3$, $CONHNHR_3$, $CH_2OR_3$, $CH_2NHR_3$, and $CH_2R_3$;

$R_3$, $R_4$ and $R_6$ are each independently selected from:

hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

$R_5$ is selected from the group consisting of O, S and NH; and $R_7$, $R_8$ and $R_9$ each are independently selected from:

hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;

a glycosyl group wherein said glycosyl group is selected from the group consisting of ribosyl, 2'-deoxyribosyl, 2'3'-dideoxy-3'-azidoribosyl, 2'3'-dideoxy-2'-fluororiboxyl, 2',3'-dideoxy-3'-fluororibosyl, 2',3'-dideoxy-2',3'-difluororiboxyl, and mono-, di- and triphosphate derivatives thereof; and $(CH_2)_m$—XR'—$(CH_2)_n$—YR' wherein R' is selected from the group consisting of:

H, $H_2$, $H_2PO_3$, $H_3P_2O_6$, $H_4P_3O_9$, and alkali metal or alkaline earth metal salts thereof;

m is zero to 20, n is zero to 20, and a is zero or one; and

U, X, Y, Z, W, J, K, and L are selected from the group consisting of C, N, O, P, and S. U, X, Y, Z, W, J, K and L may be selected from C and N.

Formula II can be 4,5,6,7-tetrahydro-8-hydroxy-8H-1-β-D-ribofuranosyl[4,5-d][1,3]diazepine-5-one wherein $R_1$ is OH, $R_2$, $R_4$, $R_6$ and $R_8$ are H, $R_5$ is O, $R_3$ is $H_2$, $R_9$ is 1-β-D-ribofuranosyl, and a for $R_7$ is zero.

Furthermore, it must be noted that the present invention includes all chiral forms and stereoisomers of the compounds presented above.

Additionally, the present invention includes non-planar, non-aromatic, ring-expanded ("fat") heterocyclic bases, nucleosides or nucleotides having the following formulas III and IV:

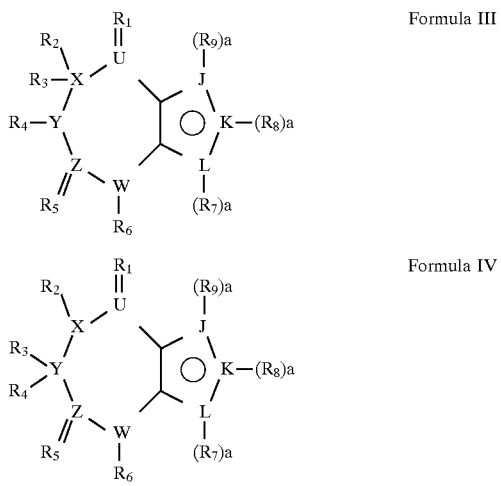

Formula III

Formula IV wherein:

$R_1$ and $R_5$ are each independently selected from O, S, and NH;

$R_3$ and $R_4$ are each independently selected from H, $OR_2$, $SR_2$, $NHR_2$, $CO_2R_2$, $CONHR_2$, $CONHNHR_2$, $CH_2OR_2$, $CH_2NHR_2$, and $CH_2R_2$;

$R_2$ and $R_6$ are each independently selected from:

hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

$R_7$, $R_8$, and $R_9$ are each independently selected from:

hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;

a glycosyl group wherein said glycosyl group is selected from the group consisting of ribosyl, 2'-deoxyribosyl, 2'3'-dideoxy-3'-azidoribosyl, 2',3'-dideoxy-2'-fluororibosyl, 2',3'-dideoxy-3'-fluororibosyl, 2',3'-dideoxy-2'3'-difluororibosyl, and mono-, di-, and triphosphate derivatives thereof;

$(CH_2)_m$—XR'—$(CH_2)_n$—YR' wherein R' is selected from:

hydrogen, $H_2PO_3$, $H_3P_2O_6$, $H_4P_3O_9$, and alkali metal or alkaline earth metal salts thereof;

m is zero to 20, n is zero to 20, and a is zero or one;

U, X, Y, Z, W, J, K, and L are selected from the group consisting of C, N, O, P, and S.

Formula (IV) may be 4,5,7,8-tetrahydro-6-hydroxy-3H, 6H-imidazo[4,5-e][1,4]diazepine-5,8-dione, wherein $R_1$ and $R_5$ are O, $R_3$ is OH, $R_2$, $R_4$, $R_6$, $R_7$ and $R_8$ are H, and a for $R_9$ is zero.

Furthermore, it must be noted that the present invention includes all chiral forms and stereoisomers of the compounds presented above.

The present invention also includes a method of treating a viral, bacterial, fungal or parasitic infection in a patient or vertebrate animal comprising administering at least one of the compounds noted above in an amount sufficient to effect the treatment.

The virus causing the infection may be selected from the group consisting of human immunodeficiency virus, Human B lymphotropic virus, Herpes simplex virus, Varicella-zoster virus, Epstein-Barr virus, necrotic rhinitis, Malignant catarrh, Allerton virus, Equine herpesviruses, Neurolymphomatosis, Influenza viruses, Parainfluenza viruses, Adenoviruses, Rheovirus, Respiratory syncytial virus, Rhinoviruses, Coxsackie virus, Echo viruses, Epidemic gastroenteritis virus, Rubeola virus, Hepatitis viruses, and Papovavirus.

The compound can be administered subcutaneously, intravenously, intramuscularly, intraperitoneally, orally, topically, or by a combination thereof.

Treatment can involve administering at least one of the compounds of the present invention in combination with at least one other known therapeutic agent.

The present invention also includes a pharmaceutical composition comprising at least one of the above-compounds and a pharmaceutically acceptable carrier.

All U.S. patents and publications referred to herein are hereby incorporated by reference.

BRIEF DESCRIPTION OF THE DRAWINGS

FIGS. I to III

Figure 1:
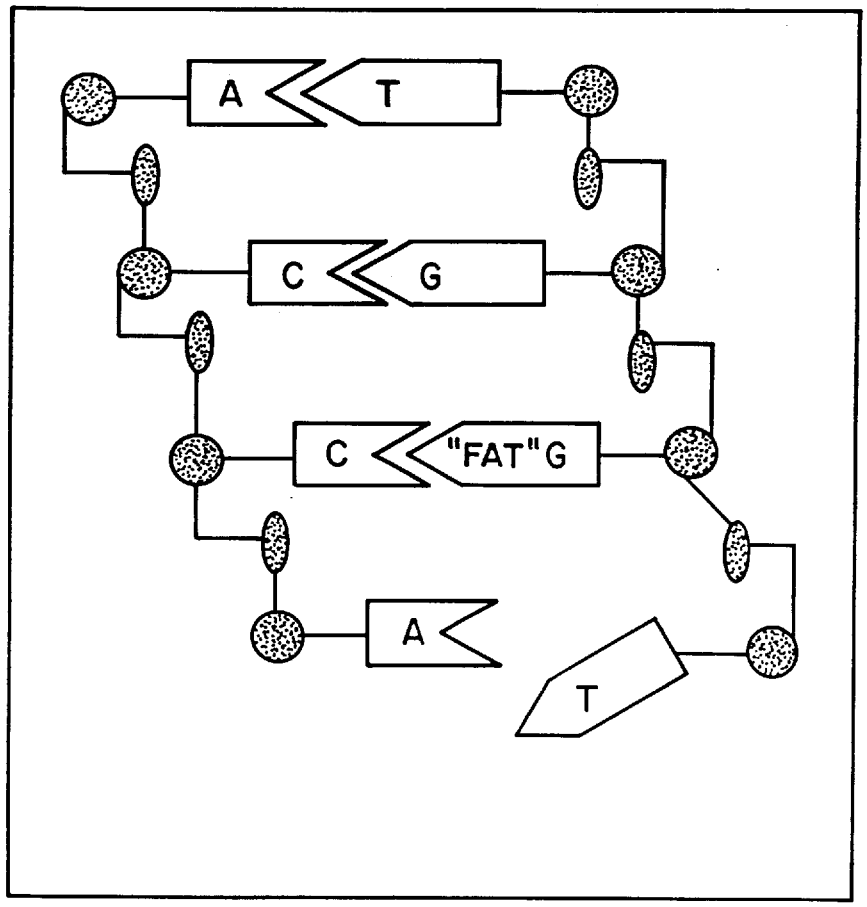

FIG. 1 shows a schematic representation of chain termination due to conformational deviation.

Figure 2A:
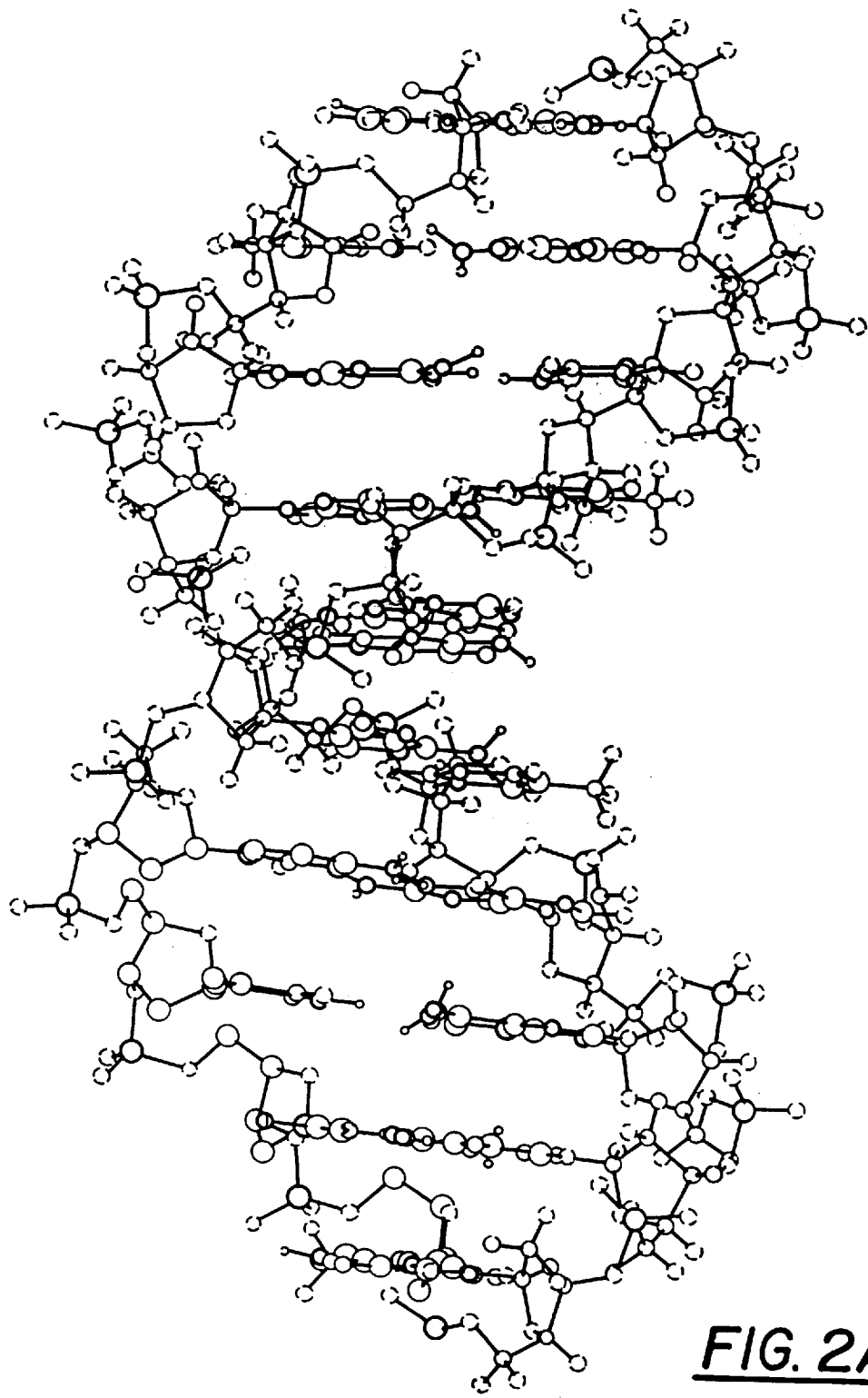
Figure 2B:
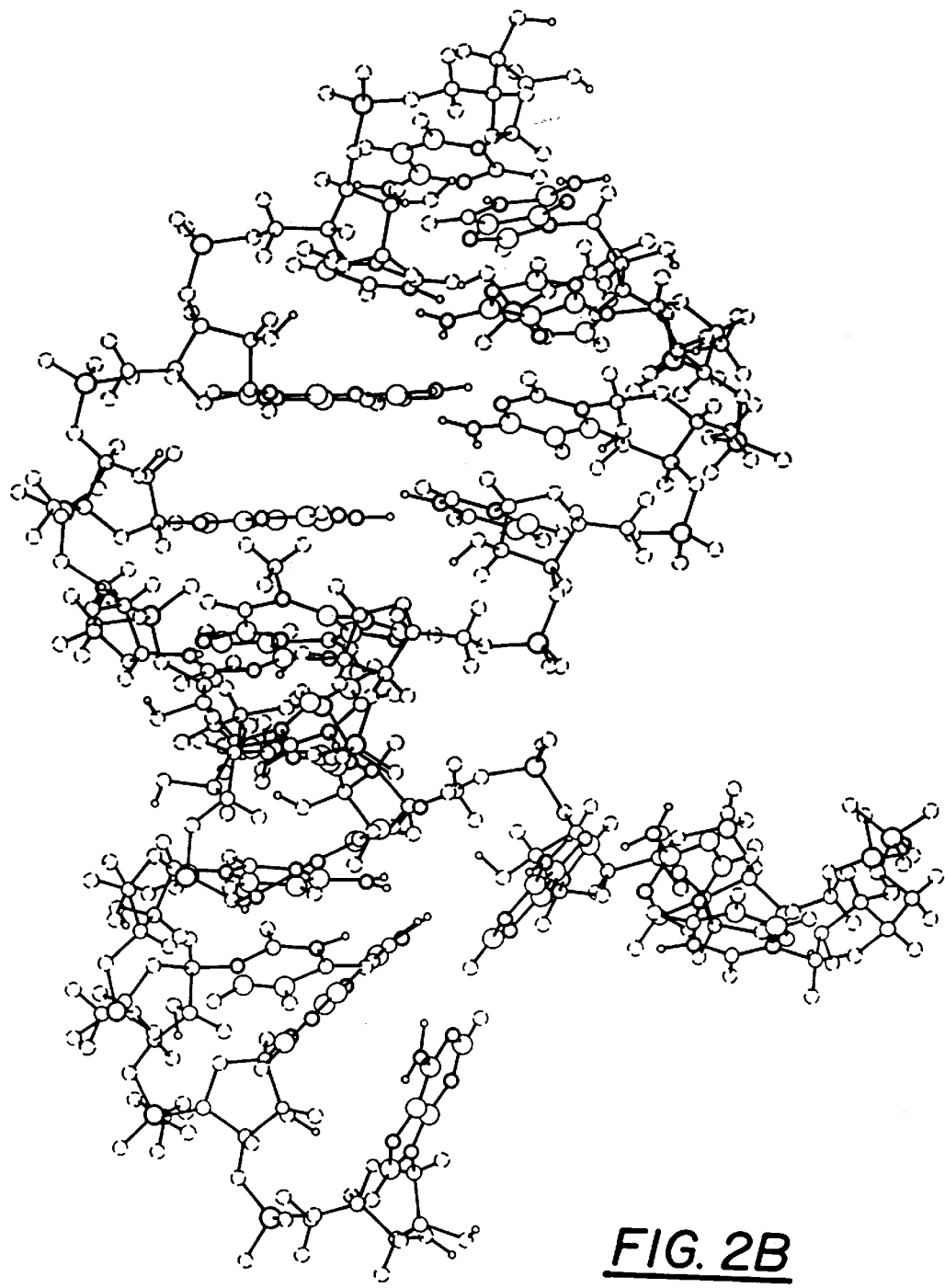
Figure 2C:

FIG. 2 represents molecular models of: (A) a duplex containing ten natural nucleotide basepairs, and (B) a duplex with nine natural nucleotide pairs present in (A) plus a "fat" guanine (fg) nucleotide at position 5 base-paired with C. (C) represents the space-filling model of (B).

Figure 3A:
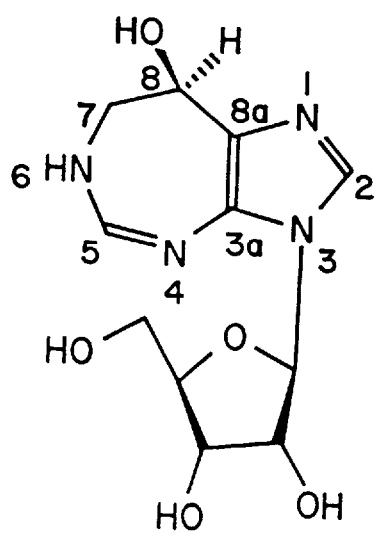
Figure 3B:
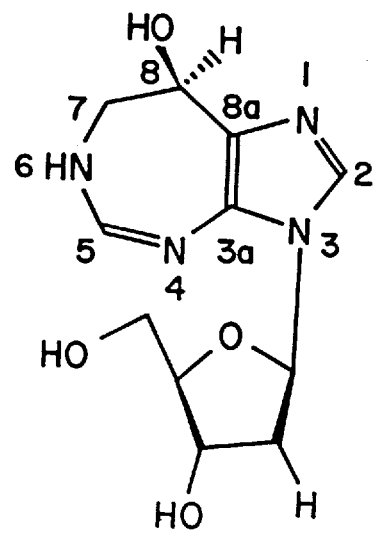
Figure 3C:
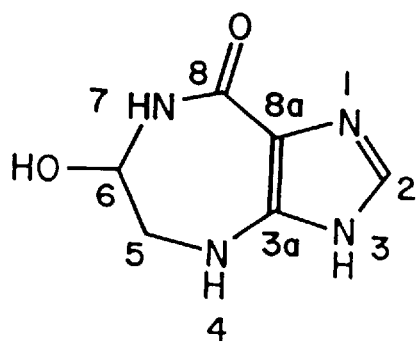

FIGS. 3A, 3B and 3C shows the chemical structures of the naturally occurring synergistic antitumor antibiotics Coformycin, Pentostatin, and Azepinomycin. These compounds have a ring-expanded heterocyclic and/or nucleoside structure.

DETAILED DESCRIPTION OF THE INVENTION

One embodiment of the present invention relates to compositions comprising planar aromatic, ring-expanded ("fat") heterocyclic bases, nucleosides or nucleotides. These bases, nucleosides or nucleotides have formulas I (A), I (B) and I (C):

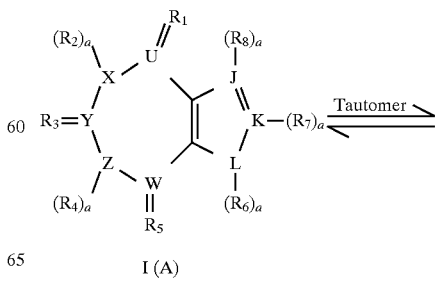

I (A)

-continued

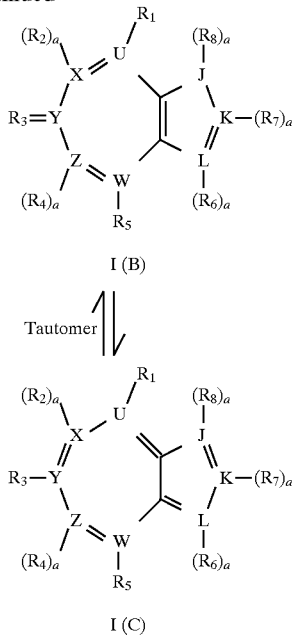

I (B)

Tautomer

I (C)

wherein:
R$_1$, R$_3$ and R$_5$ are each independently selected from:
NH, NH$_2$, O, OH, S, and SH;
NH-alkyl, N-alkyl, O-alkyl and S-alkyl wherein said alkyl group is C$_1$–C$_{20}$; NH-aryl, O-aryl and S-aryl wherein said aryl group is a substituted or unsubstituted phenyl or heterocyclic group;
N-glycosyl and NH-glycosyl wherein said glycosyl group is selected from the group consisting of ribosyl, 2'-deoxyribosyl, 2',3'-dideoxyribosyl, 2',3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di- and triphosphosphate derivatives thereof;
N—(CH$_2$)$_m$—XR'—(CH$_2$)$_n$—YR', NH—(CH$_2$)$_m$—XR'—(CH$_2$)$_n$—YR', O—(CH$_2$)$_m$—XR'—(CH$_2$)$_n$—YR' and S—(CH$_2$)$_m$—XR'—(CH$_2$)$_n$—YR' wherein R' is selected from the group consisting of hydrogen, a C$_1$–C$_{20}$ alkyl group, H$_2$PO$_3$, H$_3$P$_2$O$_6$, H$_4$P$_3$O$_9$ and the alkali metal or alkaline earth metal salts thereof;
R$_2$, R$_4$, R$_6$, R$_7$, R$_8$ are each independently selected from:
hydrogen, a C$_1$–C$_{20}$ alkyl group, an aryl group which is a substituted or unsubstituted phenyl or heterocyclic group, and an aralkyl group wherein the aryl and alkyl portions of the group have the definition given above;
a glycosyl group wherein said glycosyl group is selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-fluororibosyl, 2',3'-dideoxy-3'-azidoribosyl and mono-, di-, and triphosphate derivatives thereof;
(CH$_2$)$_m$—XR'—(CH$_2$)$_n$—YR' wherein R' is selected from the group consisting of:
hydrogen, H$_2$PO$_3$, H$_3$P$_2$O$_6$, H$_4$P$_3$O$_9$, and alkali metal or alkaline earth metal salts thereof;

m is zero to 20, n is zero to 20 and a is zero or one; and
U, X, Y, Z, W, J, K, and L are selected from the group consisting of C, N, O, P, and S.

Furthermore, it must be noted that the present invention includes all chiral forms and stereoisomers of the compounds presented above.

The compositions may also contain a "pharmaceutically acceptable carrier," for example, water, saline, Ringer's or lactated Ringer's solution, aqueous dextrose (as well as glucose, fructose, lactose, and related sugar solutions), glycols (e.g., propylene or polyethylene glycol), starch and its derivatives, fluorocarbons, cellulose derivatives, magnesium sterate, stearic acid, suitable stabilizing, buffering and preservative agents and/or other therapeutic compounds (hereinafter "pharmaceutically acceptable carrier"). Each carrier must be "acceptable" in the sense of being compatible with the other ingredients of the formulation and not injurious to the patient or recipient. Formulations with pharmaceutically acceptable carriers include those suitable for oral, rectal, nasal, topical (including buccal and sublingual), vaginal, or parenteral (including subcutaneous, intramuscular, intravenous and intradermal) administration. The formulations may be prepared in unit dosage forms and may be prepared by various methods well known in the art of pharmacy, such as bring the active ingredient into association with liquid or finely divided solid carriers which may consist of one or more accessory ingredients, and then, if necessary, shaping and coating the product.

In order to synthesize the compounds of Formula I, 4,5-dicyano- or 4,5-diacylhaloimidazole, substituted or unsubstituted at the 1-,2-, or 3-position, can be condensed with a nucleophile such as guanidine, urea or thiourea, using a polar solvent such as, for example, methanol, ethanol or acetonitrile, normally at reflux conditions. The solid separated can be filtered, dried, and recrystallized from an appropriate solvent. Further modifications of the product, such as N-, O-, or S-alkyl/aryl derivatives, can be made by standard derivatization procedures, for example, by treatment with alkyl or aryl halides. Ribosylation or deoxyribosylation can be carried out using standard glycosylation conditions that have been employed frequently in this lab (Bhan et al., *Nucleosides and Nucleotides* 11:1175 (1992); Bhadti et al., *Nucleosides and Nucleotides* 11:1137 (1992); Hosmane et al., *Nucleosides and Nucleotides* 10:1693 (1991); (Hosmane, et al., *Nucleosides and Nucleotides* 10:819 (1991); Hosmane et al., *J. Org. Chem.* 55:5882 (1990); Hosmane, et al., *Nucleosides and Nucleotides* 9:913 (1990)). The mono-, di-, and triphosphate derivatives of the nucleosides can be prepared by standard chemical (Scheit, "Nucleotide Analogs: Synthesis and Biological Function," John Wiley, New York 1980, pp. 195–218)); Petrie, et al., *J. Med. Chem.* 29:268 (1986)); Moffatt, et al., *J. Am. Chem. Soc.* 83:649 (1961)) or enzymic (Leonard et al., *Biochemistry* 17:3677 (1978); Frieden, et al., *Biochem. Biophys. Res. Commun.* 91:278 (1979)) methods of phosphorylation. (Hosmane et al., *J. Org. Chem.* 55:5882 (1990)).

Another embodiment of the present invention relates to compositions comprising non-planar, non-aromatic, ring-expanded ("fat") heterocyclic bases, nucleosides or nucleotides. These bases, nucleosides or nucleotides have the following formulas (II), (III), and (IV):

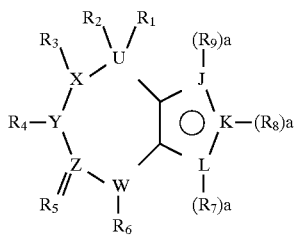

Formula II wherein, in formula II:

R₁ and R₂ are each independently selected from H, OR₃, SR₃, NHR₃, CO₂R₃, CONHR₃, CONHNHR₃ CH₂OR₃, CH₂NHR₃, and CH₂R₃;

R₃, R₄ and R₆ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

R₅ is selected from the group consisting of O, S and NH; and

R₇, R₈ and R₉ each are independently selected from:
hydrogen, a $C_1$–$C_{20}$ alkyl group, an aryl group which is a substituted or unsubstituted
hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;
a glycosyl group wherein said glycosyl group is selected from the group consisting of ribosyl, 2'-deoxyribosyl, 2',3'-dideoxy-3'-azidoribosyl, 2',3'-dideoxy-2'-fluororibosyl, 2'3'-dideoxy-3'-fluororibosyl, 2',3-dideoxy-2',3'-difluororibosyl, and mono-, di- and triphosphate derivatives thereof; and
$(CH_2)_m$—XR'—$(CH_2)_n$—YR' wherein R' is selected from the group consisting of:
H, H₂, H₂PO₃, H₃P₂O₆, H₄P₃O₉, and alkali metal or alkaline earth metal salts thereof;
m is zero to 20, n is zero to 20 and a is zero or one; and
U, X, Y, Z, W, J, K, and L are selected from the group consisting of C, N, O, P, and S.

Furthermore, it must be noted that the present invention includes all chiral forms and stereoisomers of the compounds presented above.

Additionally, the present invention includes non-planar, non-aromatic, ring-expanded ("fat") heterocyclic bases, nucleosides or nucleotides having the following formulas III and IV:

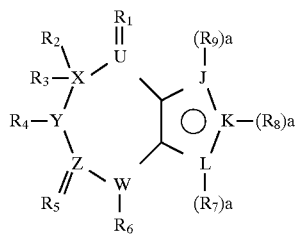

Formula III

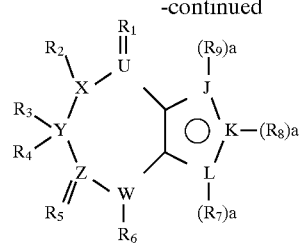

Formula IV wherein:

R₁ and R₅ are each independently selected from O, S, and NH;

R₃ and R₄ are each independently selected from H, OR₂, SR₂, NHR₂, CO₂R₂, CONHR₂, CONHNHR₂, CH₂OR₂, CH₂NHR₂, and CH₂R₂;

R₂, R₄ and R₆ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

R₇, R₈, and R₉ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;
a glycosyl group wherein said glycosyl group is selected from the group consisting of ribosyl, 2'-deoxyribosyl, 2'3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di-, and triphosphate derivatives thereof;
$(CH_2)_m$—XR'—$(CH_2)_n$—YR' wherein R' is selected from:
hydrogen, H₂PO₃, H₃P₂O₆, H₄P₃O₉, and alkali metal or alkaline earth metal salts thereof;
m is zero to 20, n is zero to 20, and a is zero or one; and
U, X, Y, Z, W, J, K, and L are selected from the group consisting of C, N, O, P, and S.

The compositions relating to formulas (II), (III) and (V) may also contain a pharmaceutically acceptable carrier.

Furthermore, it must be noted that the present invention includes all chiral forms and stereoisomers of the compounds presented above.

The synthesis of all compounds start from the common starting material 5-nitroimidazole-4-carboxylic acid that may or may not be substituted at the 1-, 2-, or 3-position. The acid group can be converted into an activated ester, normally by treatment with 1,1'-carbonyldiimidazole (CDI), 1,3-dicyclohexylcarbodiimide (DCC), or N-hydroxysuccinimide. The activated ester can be further condensed with an anion of, for example, nitromethane (Formula II), an anion of, for example, dimethyl or diethyl nitromalonate (Formula III), or, for example, dimethyl or diethylaminomalonate (Formula IV). Catalytic reduction of the two nitro groups of the product of the above nitromethane condensation, using a reagent such as tin chloride, followed by base-catalyzed ring-closure can give the 5:7-fused heterocyclic precursors of compounds of general Formula II. Subsequent reduction of these dicarbonyl precursors with a reagent, for example, sodium borohydride can specifically reduce the keto carbonyl while leaving the ureido carbonyl group intact, thus affording the desired compounds of general formula II.

With respect to compounds of general Formula III, the product of the above dialkyl nitromalonate condensation can be subjected to sequential hydrolysis, decarboxylation, and reesterification to obtain 2-alkoxycarbonyl-2-(5-nitroimidazolyl-4-carbonyl)nitromethane derivatives. The activated methane group of the side chain can now be exploited to introduce a leaving group such as bromide which can be subsequently converted into an alkoxy group. Catalytic reduction of the two nitro groups, followed by ring-closure, in a manner analogous to the one described above for Formula II, can afford the 5:7-fused heterocyclic precursors of Formula III. In the final step, the alkoxy group can be hydrolyzed to the corresponding hydroxy group to afford the desired compounds of general Formula III. The methodology to be used for compounds of Formula IV is very similar to that of Formula III except that the initial condensation product has a carbonylaminomalonate side chain. The procedures to be employed for the preparation of alkyl, aryl and nucleoside/nucleotide derivatives are analogous to the ones described above for compounds of general Formula I.

The compounds of the present invention exhibit antiviral activity with acceptable levels of cytotoxicity and can thus be used either singly or in combination to maximize therapeutic effectiveness in the treatment of viral, bacterial, fungal, parasitic or other infections. Viruses contemplated to be within the broad scope of treatment of the present invention include, but are not limited to, the following: Human Immunodeficiency virus (HIV), Human B lymphotropic virus, Herpes simplex virus, Varicella-zoster virus, Epstein-Barr virus, necrotic rhinitis, Malignant catarrh, Allerton virus, Equine herpesviruses, Neurolymphomatosis, Influenza viruses, Parainfluenza viruses, Adenoviruses, Rheovirus, Respiratory syncytial virus, Rhinoviruses, Coxsackie virus, Echo viruses, Epidemic gastroenteritis virus, Rubeola virus, Hepatitis viruses, and Papovavirus.

The compounds of this invention can be administered for the treatment of any disease or any applicable medical or non-medical condition by any means that effects contact of the active ingredient compound with the site of action in the body of a warm-blooded animal or cold-blooded antimal, plant (for agricultural uses), or lower forms of life (i.e., invertebrates, bacteria, single-celled organisms, and cell or tissue culture, among others). For the purpose of this disclosure, a warm-blooded animal is a member of the animal kingdom having a homeostatic mechanism and includes, for example, mammals and birds. For example, administration can be parenteral, i.e., subcutaneous, intravenous, intramuscular, or intraperitoneal. Alternatively, or concurrently, in some cases, administration can be by the oral or topical route.

The compounds of this invention are suitable for treating dermatological complaints relating to viral, bacterial, fungal, immunologic, and/or keratinization disorders (e.g., differentiation—proliferation disorders, including psoriasis). The topical compositions are advantageously in the form of ointments, salves, tinctures, creams, emulsions, solutions, lotions, sprays, powders, gels, suspensions, patches or saturated pads. The compounds are mixed with inert, nontoxic, generally liquid or pasty bases which are suitable for treatment by a topical route with concentrations of active compound(s) ranging from 0.0005% to 5% by weight. It is possible, of course, to employ higher concentrations when this is required for a particular therapeutic application; however, the preferred concentrations of active compound(s) are from 0.002 to 1% by weight. When the compound(s) of the invention are administered by an ocular route, they are advantageously presented in the form of a solution or a powder to be diluted to give an eye lotion.

Certain compounds which are encompassed by the present invention are metabolic inhibitors and can be administered with anti-tumor and/or anti-viral agents to potentiate their action by inhibiting adenosine deaminase and/or guanase enzymes. The compounds can be administered with antiviral agents in ratios of from about 0.005 to about 0.5 parts of the compound to about 1 part of antiviral agent. The pharmaceutical composition can be in bulk form or in aqueous solution with other materials such as preservatives, buffering agents, agents intended to adjust the osmolality of the solution, etc.

From a medicinal standpoint, the compounds of the present invention can also be regarded as analogues of the well-studied benzodiazepines and benzotriazepines, a family of powerful pharmaceuticals (e.g., valium) acting on the central nervous system (Coffen et al., *J. Org. Chem.* 49:296 (1984) and references cited therein), and may also be shown to act by binding to purine receptors, regulating ion channels, affecting synaptic vesicle trafficking, and nerve signal transduction. (Recently benzodiazepine analogues have become the focus of attention because of their ability to block mutated ras genes from making cells cancerous (Travis, *Science* 260:1877 (1993); James et al., *Science* 260:1937 (1993).) In this regard, it is important to note that the recently reported and potent inhibitors of HIV reverse transcriptase belonging to the TIBO family of heterocycles contain the basic imidazobenzodiazepine nucleus (Pauwels et al., *Nature* 343:470 (1990)), which can be extended to include tricyclic analogues of the present compound. The imidazobenzodiazepine compounds are thought to be several-fold more potent and less toxic than AZT for the growth inhibition of HIV-1 (Liaw et al., *J. Am. Chem. Soc.* 113:1857 (1991). A benzodiazepine analogue has also been recently reported to be a powerful anti-Tat agent capable of blocking HIV replication in both acutely and chronically infected HIV-infected cells (Hsu et al., *Science* 254:1799 (1991)).

The compounds of the invention can be administered by any conventional means available for use in conjunction with pharmaceuticals, either as individual therapeutic agents or in a combination of therapeutic agents. They can be administered alone, but are generally administered with a pharmaceutically acceptable carrier selected on the basis of the chosen route of administration and standard pharmaceutical practice.

The dosage administered will be dependent on the age, health and weight of the recipient, the extent of disease, kind of concurrent treatment, if any, frequency of treatment, and the nature of the effect desired. Usually, a daily dosage of active ingredient compound will be from about 1–1000 milligrams per day. Ordinarily, from 10 to 500 milligrams per day in one or more applications is effective to obtain the desired results.

The active ingredient of the present invention can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules can contain the active ingredient and powdered carriers, such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration and/or respiratory inhalants preferably contain a water soluble salt of the active ingredient, suitable stabilizing agents, and if necessary buffer substances. Antioxidizing agents such a sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorbutanol.

Suitable pharmaceutical carriers are described in Remington's Pharmaceutical Sciences, A. Osol, Mack Publishing Co., Easton, Pa. (1990), a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of lactose, 50 milligrams of cellulose, and 6 milligrams of magnesium stearate.

Soft Gelatin Capsules

A mixture of active ingredient in a digestible oil such as soybean oil, cottonseed oil or olive oil is prepared and injected by means of a positive displacement pump into gelatin to form gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.25 milliliters of vanillin.

Cosmetic

The present invention also provides a cosmetic composition containing, in a cosmetically acceptable carrier, at least one compound, or its salts or isomers, the composition being, in particular, in the form of a lotion, gel, cream, soap or shampoo.

Veterinary

The compound of the invention may also be presented for use in the form of veterinary formulations prepared by conventional methods in the art. Examples of such veterinary formulations include those adapted for oral administration (drenches of aqueous or non-aqueous solutions or suspensions), tablets, boluses, powders, granules, or pellets (for feed admixtures), or pastes for application to the tongue. Other examples of such veterinary formulations include those adapted for parenteral administration (by subcutaneous, intramuscular, or intravenous injection as a sterile solution or suspension or by intramammary injections in which a solution or suspension is introduced into the udder via the teat); topical application (as a cream, ointment, dip or spray applied to the skin); or intravaginally (as a pessary, cream, or foam).

In addition to the ingredients mentioned above, including compounds of the present invention, the formulations of the invention may include other agents convention in the art in reference to the type of formulation, e.g., those suitable for oral administration may include such further agents such as sweeteners, flavoring agents, thickeners, etc. The formulations of the invention for human or veterinary use may be presented in unit-dose or multi-dose sealed containers (ampoules and vials) and may be stored in a lyophilyzed or freeze-dried form requiring the addition of a sterile liquid carrier for reconstitution immediately prior to use.

EXPERIMENTAL EXAMPLES

The present invention can be illustrated by the use of the following non-limiting examples:

EXAMPLE 1

4,8-Diamino-6-imino-1H-imidazo[4,5-e][1,3] diazepine

[Formula I(B), where U,Y,W,K=C; X,Z,J,L=N; $R_1,R_5$=$NH_2$; $R_3$=NH; $R_2,R_4,R_6$=None; and $R_7,R_8$=H]

Method A: By Condensation of 4,5-Dicyanoimidazole with Guanidine:

Guanidine was liberated from guanidine hydrochloride (1.15 g, 12 mmol) by addition of a freshly prepared solution of sodium methoxide in methanol from sodium (0.28 g, 12 mmol), and stirring with ice-water cooling for 30 minutes. The precipitated sodium chloride was filtered off, and the filtrate was added to the solution of 4,5-dicyanoimidazole (1.18 g, 10 mmol) in methanol (25 mL). The reaction mixture was heated to reflux for 20 hours and cooled to room temperature. The solid separated was collected by filtration, and recrystallized from methanol. Yield 1.15 g (65%), mp>220 C: $^1$H NMR (DMSO-$d_6$) δ 7.75 (s, 2 H, $NH_2$, exchangeable with $D_2O$); 7.65 (s, 2 H, $NH_2$, exchangeable with $D_2O$), 7.53 (s, 1 H, imidazole CH), 6.98 (s, 2 H, two NH, exchangeable with $D_2O$); $^{13}$C NMR (DMSO-$d_6$) δ 164 (C=NH), 160 (C=N), 150 (C=C), 136.5 (imidazole CH); IR (KBr) 3300, 3010 $cm^{-1}$.

Anal. Calcd. for $C_6H_7N_7$: C, 40.68; H, 3.98; N, 55.34. Found: C, 40.67; H, 4.02; N, 55.28.

Method B: By Debenzylation of 4,8-Diamino-1-benzyl-6-iminoimidazo[4.5-e][1,3]diazepine

[Formula I(B), where U,Y,W,K=C; X,Z,J,L=N; $R_1,R_5$=$NH_2$; $R_3$=NH; $R_2,R_4,R_6$=None; and $R_7$=H; $R_8$=$CH_2$Ph)]:

4,8-Diamino-1-benzyl-6-iminoimidazo[4,5-e][1,3]diazepine (0.54 g, 2 mmol) was dissolved in glacial acetic acid (15 mL) in a hydrogenation bottle. Palladium hydroxide on carbon (20%, 80 mg) was added to the above solution, and the mixture was hydrogenated in a Parr hydrogenator at 40 psi for 16 hours. The catalyst was removed by filtration through Celite, and was washed with acetic acid (5 mL). The filtrate, along with the washings, was evaporated to dryness under reduced pressure to obtain a colorless residue. The residue was dissolved in cold water, filtered, and the filtrate was evaporated under reduced pressure. The resulting white solid was recrystallized from water. Yield 0.2 g, 56%.

The spectral and analytical data of this compound were consistent with those of the compound obtained above by Method A.

EXAMPLE 2

6-Imino-1H-imidazo[4,5-e][1,3]diazepine-4,8-dione [Formula I(A), where U,Y,W,K=C; X,Z,J,L=N; $R_1$, $R_5$=O; $R_3$=NH; $R_2,R_4,R_6,R_7$=H; $R_8$=None]

(a) 4,5-Imidazolediformyl Chloride: 4,5-imidazoledicarboxylic acid (2.0 g, 12.8 mmol) was placed in a flame-dried three-necked, round-bottomed flask, fitted with a $CaCl_2$ guard tube. Thionyl chloride (10 mL, 0.137 mol) was introduced through a serum cap, and the reaction mixture was heated at 50° C. with continuous stirring for 24 hours. The reddish-yellow reaction mixture was rotary evaporated to dryness under anhydrous conditions, and the residue was coevaporated to dryness with dry toluene (3×10 mL). The resultant residue was employed for the next step given below without further purification.

(b) 6-Imino-1H-imidazo[4,5-e][1, 3]diazepine-4,8-dione: Guanidine was liberated from guanidine hydrochloride (0.955 g, 10 minol) by addition of a freshly prepared solution of sodium methoxide in methanol from sodium (0.23 g, 10 mmol), and stirring with ice-water cooling for 30 minutes. The precipitated sodium chloride was filtered off, and the filtrate was added to the solution of 4,5-imidazolediformyl chloride, prepared from the above step, in methanol (20 mL). The reaction mixture was heated to reflux for 20 hours and cooled to room temperature. The solid separated was collected by filtration, and recrystallized from water. Yield 1.7 g (79%) mp>220° C.: $^1$H NMR (DMSO-$d_6$) δ 7.68 (s, 1 H, imidazole CH), 7.02 (br s, 4 H, four NH, exchangeable with $D_2O$); $^{13}$C NMR (DMSO-$d_6$) δ 164 (C=O), 158.5 (C=NH), 137 (C=C), 133 (imidazole CH); IR (KBr) 3470, 3400, 3200, 3090, 1720, 1680, cm$^{-1}$.

The compound gave positive test with 1M $AgNO_3$ solution, precipitating AgCl, indicating that the compound was a hydrochloride salt.

Anal. Calcd. for $C_6H_5N_5O_2.2H_2O$: C, 33.46; H, 4.18; N, 32.54 Found: C, 33.49; H, 4.23; N, 32.47.

EXAMPLE 3

4,8-Diamino-1-benzyl-6-iminoimidazo[4,5-e][1,3]diazepine

[Formula I(B), where U,Y,W,K=C; X,Z,J,L=N; $R_1,R_5$=$NH_2$; $R_3$=NH; $R_2$, $R_4$, $R_6$=None; $R_7$=H; and $R_8$=$CH_2Ph$]

(a) 1-Benzyl-4,5-dicyanoimidazole: 4,5-Dicyanoimidazole (5.0 g, 42 mmol) was placed in a 250-mL three-necked, round-bottomed flask, equipped with a magnetic stirrer, a reflux condenser, a thermometer, and a $CaCl_2$ guard tube. The solid was dissolved by addition of dimethylformamide (100 mL) with stirring. Anhydrous potassium carbonate (7.5 g, 54 mmol) was added slowly while stirring, followed by the addition of benzyl chloride (6.2 mL, 53 mmol), and the mixture was stirred at room temperature overnight. Then, the reaction mixture was heated to 75° C. and was allowed to stir at that temperature for 20 hours. The reaction mixture was cooled to room temperature, filtered to remove inorganic salts, and the filtrate was rotary evaporated to dryness. The residue was cooled in an ice-water bath, and the light yellow solid that separated was recrystallized from benzene. Yield 5.6 g (64%), mp 123–125 C: $^1$H NMR (DMSO-$d_6$) δ 8.57 (s, 1 H, imidazole CH), 7.46–7.30 (m, 5 H, Ph-H), 5.52 (s, 2 H, $CH_2$); $^{13}$C NMR (DMSO-$d_6$) δ 145 (imidazole CH), 135 (i-C of Ph), 130 (o-C of Ph), 129 (p-C of Ph), 128 (m-C of Ph), 124 (C=C), 113 (C=C), 114 (CN), 109 (CN), 51 ($CH_2$); IR (KBr) 3100, 3020, 2200, 1560–1400, 1108, 902, 840, 800, 720, 690 cm$^{-1}$; UV (MeOH) $\lambda_{max}$ 246, 207 nm.

(b) 4,8-Diamino-1-benzyl-6-iminoimidazo[4,5-e][1,3]diazepine: Guanidine hydrochloride (1.15 g, 12 mmol) was added to a solution of sodium methoxide, freshly prepared by dissolving clean sodium metal (0.28 g, 12 mmol) in absolute methanol, and the mixture was stirred in an ice-water bath for 30 minutes. The precipitated sodium chloride was filtered off, and the filtrate was poured into a portion of the solution of 1-benzyl-4,5-dicyanoimidazole prepared above (2.08 g, 10 mmol) in 25 mL of methanol. The reaction mixture was heated to reflux for 20 hours, cooled to room temperature and the precipitated solid was then collected by filtration and recrystallized from methanol. Yield 2.11 g (79%), mp 202–204 C: $^1$H NMR (DMSO-$d_6$) δ 8.12 (s, 1 H, imidazole CH), 7.32–7.20 (m, 9 H, five Ph-H+two $NH_2$, exchangeable with $D_2O$), 5.83 (s, 2 H, $CH_2$); $^{13}$C NMR (DMSO-$d_6$) δ 158.2 (C=NH), 158.1 (C=N), 157.5 (C=N), 141.5 (imidazole CH), 139 (i-C of Ph), 133.2 (C=C), 133.0 (C=C), 129.5 (o-C of Ph), 128.4 (p-C of Ph), 128.2 (m-C of Ph); IR (KBr) 3320, 3200, 1650, 1580, 1520, 1500, 1420, 1380, 900, 870 cm$^{-1}$.

Anal. Calcd. for $C_{13}H_{13}N_7$: C, 58.42; H, 4.90; N, 36.68. Found: C, 58.51; H, 4.89; N, 36.58.

EXAMPLE 4

4,6,8-Triimino-1-β-D-ribofuranosylimidazo[4,5-e][1,3]diazepine

[Formula I(A), where U,Y,W,K=C; X,Z,J,L=N; $R_1,R_3$, $R_5$=NH; $R_2,R_4,R_7$=H; $R_6$=1-β-D-Ribofuranosyl; and $R_8$ =None]

Method A: By Condensation of 4,5-Dicyano-1-β-D-ribofuranosylimidazole with Guanidine:

(a) 1-(2,3,5-Tri-O-benzoyl-β-D-ribofuranosyl)-4,5-dicyanoimidazole: A solution of 4,5-dicyanoimidazole (354 mg, 3.0 mmol) and 1-O-acetyl-2,3,5-tri-O-benzoyl-β-D-ribofuranose (1.51 g, 3 mmol) in acetonitrile (30 mL) was charged to a flame-dried, three-necked, 50-mL round-bottomed flask, equipped with a refluxing condenser, a magnetic stirrer, and a $N_2$ gas inlet. The solution was stirred in an ice-water bath for 5 minutes. Freshly distilled hexamethyldisilazane (HMDS) (0.7 mL, 3.3 mmol), freshly distilled chlorotrimethylsilane (CTMS) (0.45 mL, 3.6 mmol), and trifluoromethanesulfonic acid (TFMSA) (0.3 mL, 3.6 mmol) were consecutively added to the above solution. The resulting solution was stirred in an ice-water bath for 30 minutes. The reaction, as monitored by TLC (silica gel, toluene:acetic acid:water=5:5:1), showed complete conversion to the product in 30 minutes. Methylene chloride (30 mL) was added to the reaction mixture and was extracted with saturated aqueous NaHCO$_3$. The organic layer was separated, and the aqueous layer was once again extracted with CH$_2$Cl$_2$ (10 mL). The combined organic extracts were washed with saturated aqueous NaCl, dried over anhydrous MgSO$_4$, filtered, and the filtrate was evaporated to dryness under reduced pressure to obtain a foam. Yield 1.5 g (94%), mp 68–72 C: $^1$H NMR (DMSO-d$_6$) δ 8.68 (s, 1 H, imidazole CH), 7.92 (m, 5 H, Ph-H), 7.63 (m, 5 H, Ph-H), 7.40 (m, 5 H, Ph-H), 6.63 (d, J=4.8 Hz, 1 H, H-1'), 6.06 (t, J=5.1 Hz, 1 H, H-2'), 5.99 (t, 1 H, H-3'), 4.97 (q, 1 H, H-4'), 4.74 (dd, 2 H, H-5'); $^{13}$C NMR (DMSO-d$_6$) δ 163 (C=O), 161 (C=O), 160.5 (C=O), 142.6 (imidazole CH), 135 (Ph-C), 134.8 (Ph-C), 134.4 (Ph-C), 130.4 (Ph-C), 130.2 (Ph-C), 130.0 (Ph-C), 129.8 (Ph-C), 129.7 (Ph-C), 129.5 (Ph-C), 129.4 (Ph-C), 129.3 (Ph-C), 129.0 (Ph-C), 124 (C=C), 113 (C≡N), 111.7 (C≡N), 109.2 (C=C), 89.8 (C-1'), 81.8 (C-2'), 75.5 (C-3'), 71.5 (C-4'), 64.2 (C-5').

Anal. Calcd. for C$_{31}$H$_{22}$N$_4$O$_7$: C, 66.19; H, 3.94; N, 9.96. Found: C, 66.20; H, 3.96; N, 9.76.

(b) 4,6,8-Triimino-1-β-Dribofuranosylimidazo[4,5-e][1,3]diazepine: 1-(2,3,5-Tri-O-benzoyl-β-D-ribofuranosyl)-4,5-dicyanoimidazole (2.0 g, 3.5 mmol) was added to a cold solution of sodium methoxide solution freshly prepared by dissolving sodium metal (2.0 g, 86.95 mg.atom) in 50 mL of methanol. Guanidine hydrochloride (3.5 g, 36 mmol) was then added. The reaction mixture was heated at reflux overnight. A tlc of the reaction mixture (silica gel, CHCl$_3$:MeOH, 4:1) indicated complete consumption of the starting material and the presence of a new, UV-absorbing spot which had a lower Rf than the starting material. The reaction mixture was cooled and acidified to pH 6.5 with 1N HCl. The solution was mixed with flash silica gel (4 g, particle size 40–63 μm) and rotary evaporated to dryness. The silica gel-adsorbed compound was purified by flash chromatography on a column of flash silica gel of the same particle size as above. Elution with a mixture of CHCl$_3$:MeOH (4:1) removed most of the impurities present. The column was then eluted with methanol alone, and the appropriate UV-absorbing fractions were pooled and evapored to afford a solid which was recrystallized from 2-propanol to give white powder. Yield 0.45 g (40%), mp>200 C: $^1$H NMR (DMSO-d$_6$) δ 8.76 (br s, 1 H, exchangeable with D$_2$O, NH), 8.60 (s, 1 H, imidazole CH), 8.56 (s, 1 H, exchangeable with D$_2$O, NH), 8.46 (s, 1 H, exchangeable with D$_2$O, NH), 8.20 (s, 1 H, exchangeable with D$_2$O, NH), 8.17 (s, 1 H, exchangeable with D$_2$O, NH), 6.35 (br s, 1 H, exchangeable with D$_2$O, ribose OH), 6.0 (d, 1 H, J=6.3 Hz, anomeric H), 5.43 (d, 1 H, J=4.5 Hz, exchangeable with D$_2$O, ribose OH), 5.25 (t, 1 H, J=5.4 Hz, exchangeable with D$_2$O, ribose OH), 4.35 (t, 1 H, H-2'), 4.06 (m, 2 H, H-3' and H-4'), 3.64 (m, 2 H, H-5'); $^{13}$C NMR (DMSO-d$_6$) δ 163.94 (C=N), 157.79 (C=N), 152.16 (C=N), 140.52 (C=C), 138.13 (C=N), 126.58 (C=C), 89.31 (ribose C), 87.41 (ribose C), 76.27 (ribose C), 70.65 (ribose C), 61.03 (ribose C); MS (FAB) 310 (MH$^+$).

Anal. Calcd. for C$_{11}$H$_{15}$N$_7$O$_4$.2HCl: C, 34.71; H, 4.47; N, 25.77. Found: C, 34.87; H, 4.54; N, 25.70.

Method B: By Ribosylation of 4,8-Diamino-6-imino-1H-imidazo[4,5-e][1,3]diazepine (a) 1-(2,3,5-Tri-O-benzoyl-β-D-ribofuranosyl)-4,6,8-triiminoimidazo[4,5-e][1,3]diazepine. 4,8-diamino-6-imino-1H-imidazo[4,5-e][1,3]diazepine (see Example 1 above) (1.0 g, 5.6 mmol) was placed in a dry, three-necked, round-bottomed flask, fitted with a reflux condenser and a N$_2$ gas inlet. Bis(trimethylsilyl) trifluoroacetamide (BSTFA) (13.5 g, 52 mmol) was added, and the reaction mixture was heated at reflux for 2.5 hours, at which time a clear solution was formed. The solution was cooled to room temperature and evaporated to dryness in vacuo using a Küigelrohr apparatus. The residue was suspended in dry acetonitrile (50 mL), and the reaction mixture was kept at −42° C. using an acetonitrile-dry ice bath. 1-O-Acetyl-2,3,5-tri-O-benzoyl-β-D-ribofuranose (2.84 g, 5.6 mmol) was added to the reaction mixture, followed by trimethylsilyl trifluoromethanesulfonate (TMS triflate) (1.4 mL, 6.9 mmol). The reaction mixture was slowly allowed to come to 0° C. The reaction mixture was poured into 200 mL of methylene chloride and washed with 100 mL of water. The organic layer was separated and dried over anhydrous magnesium sulfate. Evaporation of the solvent afforded a residue which was triturated with 2-propanol to form a foam. An analytical sample of the foam was prepared by using diethyl ether. Yield 4.1 g (94%): $^1$H NMR (DMSO-d$_6$) δ 8.74 (s, 1 H, imidazole CH), 8.58 (s, 1 H, NH, exchangeable with D$_2$O), 8.52 (s, 1 H, NH, exchangeable with D$_2$O), 8.21 (br s, 1 H, NH, exchangeable with D$_2$O), 7.77 (m, 16 H, three Ph+one NH exchangeable with D$_2$O), 6.78 (d, J=3.0 Hz, 1 H, anomeric H), 6.22 (t, J=3.9 Hz, 1 H, ribose CH), 6.0 (t, 1 H, ribose CH), 4.93 (m, 1 H, ribose CH), 4.69 (m, 2 H, H-5').

Anal. Calcd. for C$_{32}$H$_{27}$N$_7$O$_7$.CF$_3$SO$_2$OH: C, 51.32; H, 3.62; N, 12.70. Found: C, 51.68; H, 3.87; N, 12.70.

(b) 4,6,8-Triimino-1-β-D-ribofuranosylimidazo[4,5-e][1,3]diazepine. To a solution of sodium methoxide that was freshly prepared by dissolving cleanly cut sodium metal (100 mg, 4.3 g.atom) in 100 mL of methanol, was added 1-(2,3,5-tri-O-benzoyl-β-D-ribofuranosyl)-4,6,8-triiminoimidazo[4,5-e][1,3]diazepine, prepared above (1.5 g, 1.94 mmol), at −42° C., using dry ice-acetonitrile bath. The compound dissolved slowly, and the temperature was gradually raised to 0° C. The reaction mixture was stirred at 0° C. for 4 hours when a tlc (silica gel, CHCl$_3$:MeOH, 4:1) indicated no starting material. The reaction mixture was neutralized with 1N HCl to pH 6–6.5, followed by evaporation to dryness on a rotary evaporator. The solid residue was extracted with a mixture of EtOH and MeOH (1:1), filtered, and the filtrate was evaporated to dryness. The residue was dissolved in about 3 mL of water, and to the solution was added 2-propanol when a white solid separated. The solid was filtered and was recrystallized from a mixture of 2-propanol water into colorless granules. Yield 0.68 g (92%), mp>200 C. The spectral and analytical data of this compound were consistent with those of 4,6,8-triimino-1-β-D-ribofuranosylimidazo[4,5-e][1,3]diazepine, prepared by Method A above.

EXAMPLE 5

4,5,6,7-Tetrahydro-8-hydroxy-8H-1-β-D-ribofuranosylimidazo[4,5-d][1,3]diazepine-5-one

[Formula II, where U,X,Z,K=C; Y,W,J,L=N; R$_1$=OH; R$_2$,R$_4$,R$_6$,R$_8$=H; R$_3$=H$_2$; R$_7$=None; R$_9$=1-β-D-Ribofuranosyl]

(a) 2-Amino-1-(1-benzyl-5-amino-1H-imidazol-4-yl) ethanone: 2-Amino-1-(1-benzyl-5-amino-1H-imidazol-4-yl)ethanone dihydrochloride (Baker et al., *J. Org. Chem.* 47:3457 (1982)) (900 mg, 3.0 mmol) was dissolved in H$_2$O (20 mL), and the solution was cooled in an ice-water bath. Aqueous NaOH solution (2N) was added dropwise with constant stirring until the pH of the solution reached 13–14. The solution was extracted with EtOAc (3×25 mL), and the combined extracts were dried over anhydrous MgSO$_4$. Filtration, followed by rotary evaporation of the filtrate under reduced pressure, gave a solid which was recrystallized from toluene as pale yellow crystals. Yield 400 mg (60%), mp 156–162 C: $^1$H NMR (Me$_2$SO-d$_6$) δ 7.26 (m, 6 H, Ph-H+imidazole CH), 6.5 (s, 2 H, exchangeable with D$_2$O, NH$_2$ aromatic), 5.09 (s, 2 H, benzyl CH$_2$), 3.69 (s, 2 H, side-chain CH$_2$), 1.7 (br s, 2 H, exchangeable with D$_2$O, NHz aliphatic); IR (KBr) 3400, 3360, 3260, 3100, 1650 cm$^{-1}$; mass spectrum (70 eV) m/z 230 (M$^+$), 201, 173, 91; UV (MeOH) 297 nm, (pH 13) 297.

Anal. Calcd. for C$_{12}$H$_{14}$N$_4$O: C, 62.61; H, 6.10; N, 24.35. Found: C, 63.22; H, 6.15; N, 23.26.

(b) 3-Benzyl-4,5,6,7-tetrahydro-8H-imidazo[4,5-d][1,3]diazepine-5,8-dione: A mixture of the above 2-amino-1-(1-benzyl-5-amino-1H-imidazol-4-yl)ethanone (322 mg, 1.4 mmol) and dry CH$_3$CN (30 mL) was warmed under N$_2$ in a three-necked flask, fitted with a reflux condenser and a guard tube, to form a clear solution. p Nitrophenyl-chloroformate (297 mg, 1.47 mmol) was added, whereupon a white solid separated. After addition of triethylamine (0.32 mL, 28.7 mmol), the white solid dissolved to give a clear solution. The solution was stirred at reflux for 5 hours when most of the title compound separated as a solid. The reaction mixture was cooled and the solid obtained was collected by filtration and was washed with cold CH$_3$CN, followed by Et$_2$O. The solid was recrystallized from EtOH as colorless crystals. Yield 210 mg (59%), mp 214 C dec.: $^1$H NMR (Me$_2$SO-d$_6$) δ 9.79 (s, 1 H, exchangeable with D$_2$O, NH-4), 7.63 (s, 1 H, imidazole CH), 7.3 (m, 6 H, Ph-H+NH-6, exchangeable with D$_2$O), 5.36 (s, 2 H, benzyl CH$_2$), 3.65 (d, J=4.9 Hz, 2 H, ring CH$_2$, changing to a singlet upon D$_2$O); IR (KBr) 3400, 3100, 3000, 1700, 1650 cm$^{-1}$; mass spectrum (70 eV) m/z 256 (M$^+$), 200, 91; UV (MeOH) 284.5 nm, (pH 13) 333.5.

Anal. Calcd. for C$_{13}$H$_{12}$N$_4$O$_2$. 0.25 H$_2$O: C, 59.88; H, 4.79; N, 21.49. Found: C, 60.01; H, 4.84; N, 21.59.

(c) 4,5,6,7-Tetrahydro-1H,8H-imidazo[4,5-d][1,3]diazepine-5,8-dione: The above 3-benzyl-4,5,6,7-tetrahydro-8H-imidazo[4,5-d][1,3]diazepine-5,8-dione (510 mg, 2 mmol) was dissolved in dry acetic acid (10 mL) in a Parr hydrogenation bottle. To this solution was added Pd(OH)$_2$ on carbon (20%, 80 mg), and the mixture was hydrogenated in a Parr hydrogenator at 40 psi for 16 hours. The catalyst was removed by filtration through Celite and washed with acetic acid (5 mL). The filtrate, along with the washings, was evaporated to dryness under reduced pressure to obtain a colorless residue. It was triturated with cold water, and the solid which separated was collected by filtration. It was recrystallized from water as colorless crystals. Yield 275 mg (83%), mp>300 C: $^1$H NMR (Me$_2$SO-d$_6$) δ 12.88 (br s, 1 H, exchangeable with D$_2$O, NH-1), 9.75 (s, 1 H, exchangeable with D$_2$O, NH-4), 7.74 (s, 1 H, imidazole CH), 7.14 (br s, 1H, exchangeable with D$_2$O, NH-6), 3.65 (d, J=4.5 Hz, 2 H, ring CH$_2$, changing to a singlet upon D$_2$O); IR (KBr) 3350–2950, 1750–1650 cm$^{-1}$; mass spectrum (70 eV) m/z 166 (M$^+$), 138, 110, 83; UV (H$_2$O) 278.5 nm, (pH 13–14) 304.0.

Anal. calcd. for C$_6$H$_6$N$_4$O$_2$: C, 43.38; H, 3.64; N, 33.72. Found: C, 43.29; H, 3.65; N, 33.66.

(d) 3- and 1-(2,3,5-Tri-O-benzoyl-β-D-ribofuranosyl)-4,5,6,7-tetrahydro-8H-imidazo[4,5-d][1,3]diazepine-5,8-dione: A mixture of the above 4,5,6,7-tetrahydro-1H,8H-imidazo[4,5-d][1,3]diazepine-5,8-dione (500 mg, 3 mmol) and 1-O-acetyl-2,3,5-tri-O-benzoyl-β-D-ribofuranose (1.51 g, 3 mmol) in dry CH$_3$CN (30 mL) was stirred at room temperature for 10 minutes, under N$_2$, in a three-necked flask equipped with a reflux condenser and a guard tube filled with anhydrous CaCl$_2$/CaSO$_4$. Freshly distilled 1,1,1,3,3,3-hexamethyldisilazane (0.7 mL, 3.6 mmol) and trifluoromethanesulfonic acid (0.3 mL, 3.6 mmol) were added consecutively to the above mixture whereupon it became slightly warm. The reaction was monitored by TLC (toluene:acetic acid:water=5:5:1). After stirring for 1 hour at room temperature, the TLC showed partial completion of the reaction. The reaction mixture was heated at reflux for 2 hours to obtain a clear solution whose TLC showed two different UV-absorbing spots. The solution was cooled, CH$_3$CN (10 mL) and CH$_2$Cl$_2$ (30 mL) were added, and the mixture was extracted with saturated aqueous solution of NaHCO$_3$. The organic layer was separated, the aqueous layer was once again extracted with CH$_2$Cl$_2$ (10 mL), and the combined organic extracts were washed with a saturated aqueous solution of NaCl. The organic layer was dried over anhydrous MgSO$_4$, filtered, and the filtrate was evaporated to dryness under reduced pressure to obtain a solid.

The above-solid, a mixture of two compounds, was dissolved in CH$_2$Cl$_2$ (10 mL), and the solution was mixed with silica gel (40–63 μm, 2 g) and rotary evaporated to dryness. The residue was suspended in CH$_2$Cl$_2$ (10 mL), and the resulting slurry was loaded onto a flash chromatography column packed with silica gel (40–63 μm, 100 g) in CH$_2$Cl$_2$. The column was eluted with a mixture of CH$_2$Cl$_2$-EtOAc (1:1) (250 mL) at 10 mL/min at 6 psi, followed by a mixture of EtOAc-isopropanol (9:1) (200 mL). The appropriate UV-absorbing fractions were pooled and evaporated to dryness. The residue was triturated with EtOAc, and the colorless solid obtained was collected by filtration. It was further purified by recrystallization from CH$_2$Cl$_2$-petroleum ether (40°–60° C.) to obtain colorless crystals of 1-(2,3,5-tri-O-benzoyl-β-D-ribofuranosyl)-4,5,6,7-tetrahydro-8H-imidazo[4,5-d][1,3]diazepine-5,8-dione. Yield 525 mg (35%), mp 239 C: $^1$H NMR (Me$_2$SO-d$_6$) δ 9.94 (d, J=1.95 Hz, 1 H, exchangeable with D$_2$O, NH-4), 8.23 (s, 1 H, imidazole CH), 7.63 (m, 16 H, Ph-H+NH-6, exchangeable, with D$_2$O), 6.69 (d, J=2.7 Hz, 1 H, anomeric H), 5.95 (s, 2 H, ribose-H), 4.8 (s, 3 H, ribose-H), 3.65 (d, J=4.8 Hz, 2 H, ring CH$_2$, singlet upon D$_2$O exchange).

Anal. Calcd. for C$_{32}$H$_{26}$N$_4$O$_9$.1/2 H$_2$O: C, 62.03; H, 4.39; N, 9.04. Found: C, 62.05; H, 4.17; N, 9.02.

The column was further eluted with EtOAc-isopropanol (4:1) at 10 mL/min at 6 psi. The fractions collected were found to be a mixture of two compounds. All the fractions were pooled and evaporated to dryness under reduced pressure. The residue obtained was dissolved in CHCl$_3$ (2 mL) and loaded onto a Chromatotron™ plate (1 mm thickness, Kieselgel 60 GF$_{254}$). It was eluted with a mixture of CHCl$_3$-MeOH (4:1). The appropriate UV-absorbing fractions were pooled and rotary evaporated to dryness to obtain 3-(2,3,5-tri-O-benzoyl-β-D-ribofuranosyl)-4,5,6,7-tetrahydro-8H-imidazo[4,5-d][1,3]diazepine-5,8-dione as a pinkish solid. Yield 225 mg (15%), mp 252 C: $^1$H NMR (Me$_2$SO-d$_6$) δ 9.99 (s, 1 H, exchangeable with D$_2$O, NH-4), 8.02–7.40 (m, 17 H, Ph-H+imidazole CH+NH-6, exchangeable with D$_2$O), 6.63 (d, J=6.0 Hz, 1 H, anomeric H), 6.04–5.93 (m, 2 H, ribose-H), 4.79–4.68 (m, 3 H, ribose-H), 3.65 (d, J=4.8 Hz, 2 H, ring CH$_2$, singlet upon D$_2$O exchange).

Anal. Calcd. for C$_{32}$H$_{26}$N$_4$O$_9$.1H$_2$O: C, 61.14; H, 4.49; N, 8.91. Found: C, 61.39; H, 4.22; N, 8.88.

(e) 1-β-D-Ribofuranosyl-4,5,6,7-tetrahydro-8H-imidazo[4,5-d][1,3]diazepine-5,8-dione: To a well-stirred solution of the above 1-(2,3,5-tri-O-benzoyl-β-D-ribofuranosyl)-4,5,6,7-tetrahydro-8H-imidazo[4,5-d][1,3]diazepine-5,8-dione (300 mg, 0.49 mmol) in dry MeOH (15 mL) and CH$_2$Cl$_2$ (3 mL) in a 50 mL three-necked flask equipped with a reflux condenser and maintained under $N_2$, was added dropwise, a freshly prepared solution of NaOMe in MeOH (10 mL) until the pH of the solution reached 13–14 (litmus). The mixture was stirred at room temperature for 30 minutes, cooled in an ice-water bath, and carefully neutralized to pH 6–7 with acetic acid. The solvents were removed under reduced pressure, the residue was washed with $Et_2O$ and triturated with cold $H_2O$ to obtain a solid which was recrystallized from water into colorless crystals. Yield 111 mg (76%), mp 266 C (dec.): $^1$H NMR ($Me_2SO$-$d_6$) δ 9.77 (br s, 1 H, exchangeable with $D_2O$, NH-4), 8.28 (s, 1 H, imidazole CH), 7.21 (br s, 1 H, exchangeable with $D_2O$, NH-6), 6.24 (d, J=2.7 Hz, 1 H, anomeric H), 5.34 (d, J=4.9 Hz, 1 H, exchangeable with $D_2O$, ribose-OH), 5.0 (t, 2 H, exchangeable with $D_2O$, two ribose-OH), 3.65–4.05 (m, 5 H, ribose-H), 3.65 (d, J=4.6 Hz, 2 H, ring $CH_2$, singlet upon $D_2O$ exchange); UV ($H_2O$) 239.5, 291.5 nm,(pH 13) 294.0, 341.0, (pH 2) 287.5.

Anal. Calcd. for $C_{11}H_{14}N_4O_6$: C, 44.30; H, 4.73; N, 18.78. Found: C, 44.25; H, 4.74; N, 18.69.

(f) 1-β-D-ribofuranosyl-4,5,6,7-tetrahydro-8-hydroxy-8H-imidazo[4,5-d][1,3]diazepine-5-one: The above nucleoside 1-β-D-ribofuranosyl-4,5,6,7-tetrahydro-8H-imidazo[4,5-d][1,3]diazepine-5,8-dione (58 mg, 0.20 mmol) was dissolved in a mixture of MeOH:$H_2O$ (1:1), and the solution was stirred at room temperature for 10 minutes. Sodium borohydride (21 mg, 0.55 mmol) was added to the cloudy solution, and the reaction mixture was stirred at room temperature for 30 minutes to form a clear solution. The excess reducing agent was decomposed by adding dry ice. The reaction mixture was filtered, and the filtrate was evaporated to dryness to obtain a solid. Yield 45 mg (75%), mp 238 C (dec.): $^1$H NMR ($D_2O$) δ 7.56 (s, 1 H, imidazole CH), 5.61 (d, J=3.3 Hz, 1 H, anomeric H), 4.92–4.83 (m, 1 H, H-8), 3.95 (m, 2 H, H-2'+H-3'), 3.63–3.48 (m, 4 H, H-5' $CH_2$+H-7 $CH_2$ ).

EXAMPLE 6

4,5,7,8-Tetrahydro-6-hydroxy-3H,6H-imidazo[4,5-e][1,4]diazepine-5,8-dione

[Formula IV, where U,Y,Z,K=C; X,W,J,L=N; $R_1,R_5$=O; $R_3$=OH; $R_2,R_4,R_6,R_7,R_8$=H; $R_9$=None]

(a) Diethyl 2-[N-(1-benzyl-5-nitroimidazole-4-carbonyl)amino]malonate [or 1-Benzyl-4-[N((bis(ethoxycarbonyl)methyl)carbamoyl]-5-nitroimidazole]: A 250-mL three-necked, round-bottomed flask, equipped with a reflux condenser, was charged with 1-benzyl-5-nitro-4-carboxylic acid (Hosmane, et al.,*J. Heterocycl. Chem.* 27:2189 (1990)); (5.0 g, 20 mmol), 1,1'-carbonyldiimidazole (CDI) (4.5 g, 27 mmol), and dry tetrahydrofuran (THF) (150 mL). The mixture was heated at reflux for 4 hours, when a clear solution was formed. The solution was cooled to room temperature, and a freshly prepared solution of diethylaminomalonate made from its hydrochloride salt (5.71 g, 27 mmol) by treatment with triethylamine (4.0 mL, 28.7 mmol) in 100 mL of methylene chloride, was added. The reaction mixture was stirred at room temperature for 1 hour, when a tlc (silica gel, $CHCl_3$:MeOH, 8:1) showed the formation of a new compound which had a higher Rf than the starting material. The reaction mixture was evaporated to dryness on a rotary evaporator, and the residual gum was suspended in ice-water and stirred overnight on a magnetic stirrer. A pale yellow solid that separated was filtered, washed with 2×100 mL of water, and dried. The compound was recrystallized from methanol into pale yellow flakes. Yield 7.9 g (96%), mp 88 C: $^1$H NMR (DMSO-$d_6$) δ 9.27 (d, J=7.0 Hz, 1 H, exchangeable with $D_2O$, NH), 8.28 (s, 1 H, imidazole CH), 7.38–7.19 (m, 5 H, Ph-H), 5.54 (s, 2 H, benzyl $CH_2$), 5.23 (d, J=7.5 Hz, 1 H, CH), 4.22–4.14 (q, 4 H, two ester $CH_2$), 1.21–1.18 (t, 6 H, two ester $CH_3$); MS (EI) m/z 331 ($M^+$—$CO_2Et$), 303, 259, 230.

Anal. CaLcd. for $C_{18}H_{20}N_4O_7$: C, 53.48; H, 4.98; N, 13.85. Found: C, 53.50; H, 5.03; N, 13.91.

(b) Diethyl 2-Methoxy-2-[N-(1-benzyl-5-nitroimidazole-4-carbonyl)amino]malonate: A 300-mL three-necked, round-bottomed flask, equipped with a $N_2$ inlet, was charged with 150 mL of dry methanol. Clean, freshly cut sodium metal (0.5 g, 21.74 mmol) was added, and the mixture was stirred under $N_2$ atmosphere to form a clear solution. The flask was cooled in an acetone-dry ice bath to −78° C., and the above diethyl 2-[N-(1-benzyl-5-nitroimidazole-4-carbonyl)amino]malonate (5.0 g, 12.37 mmol) was added when the color of the reaction mixture changed to dark brown. Bromine (0.9 mL, 17 mmol) was introduced through a syringe when the color of the solution changed to off-white, and some solid started separating. After 1 hour, the reaction mixture was neutralized with 2N HCl to pH 6.5, and evaporated to dryness on a rotary evaporator. The residue was suspended in water and extracted with chloroform (2×250 mL). The organic layer was separated, dried over anhydrous magnesium sulfate, filtered, and the filtrate evaporated to dryness. The residue was suspended in ether and was left to stand at room temperature. The off-white solid separated was recrystallized from ether. Yield 4.7 g (88%), mp 126–127 C: $^1$H NMR (DMSO-$d_6$) δ 9.42 (s, 1 H, exchangeable with $D_2O$, NH), 8.30 (s, 1 H, imidazole CH), 7.37–7.23 (m, 5 H, Ph-H), 5.55 (s, 2 H, benzyl $CH_2$), 4.19 (q, J=7.1 Hz, 4 H, two ester $CH_2$), 3.25 (s, 3 H, OMe), 1.65 (t, J=6.9 Hz, 6 H, two ester $CH_3$).

Anal. Calcd. for $C_{19}H_{22}N_4O_8$: C, 52.53; H, 5.10; N, 12.89. Found: C, 52.47; H, 5.11; N, 12.87.

(c) Diethyl 2-Methoxy-2-[N-(5-amino-1-benzylimidazole-4-carbonyl)amino]malonate: A mixture of the above diethyl 2-methoxy-2-[N-(1-benzyl-5-nitroimidazole-4-carbonyl)amino]malonate (500 mg, 1.15 mmol) and 5% Pd-C (100 mg) in absolute methanol (100 mL) was hydrogenated in a Parr hydrogenator at 40 psi for 50 minutes. The reaction mixture was filtered through Celite, and the filtrate was evaporated to dryness. The residual syrup was purified by rotating disk chromatography on a Chromatotron™ plate, made of silica gel (particle size 15 μm, thickness 2 mm), eluting with chloroform. Appropriate UV-absorbing fractions were pooled and evaporated to afford a syrup, which upon trituration with ether, gave an off-white solid. The compound was recrystallized from ether. Yield 255 mg (55%), mp 162–163 C: $^1$H NMR (DMSO-$d_6$) δ 7.95 (s, 1 H, exchangeable with $D_2O$, NH), 7.32–7.22 (m+s, 6 H, imidazole CH+Ph-H), 6.01 (s, 2 H, exchangeable with $D_2O$, $NH_2$), 5.08 (s, 2 H, benzyl $CH_2$), 4.19 (q, J=7.0 Hz, 4 H, two ester $CH_2$), 3.18 (s, 3 H, OMe), 1.15 (t, J=7.0 Hz, 6 H, two ester $CH_3$).

Anal. Calcd. for $C_{19}H_{24}N_4O_6$: C, 56.42; H, 5.98; N, 13.85. Found: C, 56.35; H, 5.93; N, 13.82.

(d) Diethyl 2-Methoxy-2-[N-((1-benzyl-5-(benzalimino)imidazole-4-carbonyl)amino]malonate: A 500-mL round-bottomed flask was charged with the above diethyl 2-methoxy-2-[N-(5-amino-1-benzylimidazole-4-carbonyl)amino]malonate (3.0 g, 7.4 mmol) and dry benzene (300 mL). p-Toluenesulfonic acid monohydrate (190 mg, 1 mmol) was added, followed by benzaldehyde (0.82 g, 7.7 mmol). The flask was fitted with a Dean-Stark apparatus, equipped with a reflux condenser. The reaction mixture was heated gently to reflux, and the water collected in the trap was continuously removed. The color of the reaction mixture changed to light yellow. A tlc (silica gel, chloroform:acetone, 9:1) of the reaction mixture taken after 3 hours showed a new UV-absorbing compound with a higher Rf than the starting material, along with a small amount of the unreacted starting material. The reaction mixture was allowed to continue to reflux for an additional hour, cooled, and concentrated by rotary evaporation. Chloroform (200 mL) was added, followed by 10 mL of a saturated solution of aqueous sodium bicarbonate. The mixture was transferred to a separatory funnel and extracted with water (2×50 mL). The organic layer was collected, dried over anhydrous magnesium sulfate, filtered, and the filtrate evaporated to dryness to afford a syrup. Trituration of the syrup with ether provided a pale yellow solid which was recrystallized from ether. Yield 3.0 g (84%), mp 129–131 C: $^1$H NMR (DMSO-d$_6$) δ 9.2 (s, 1 H, CH), 8.7 (s, 1 H, exchangeable with D$_2$O, NH), 8.02 (s, 1 H, CH), 7.86–7.3 (m, 10 H, Ph-H), 5.31 (s, 2 H, benzyl CH$_2$), 4.21 (q, J=6.9 Hz, 4 H, two ester CH$_2$), 3.2 (s, 3 H, OMe), 1.16 (t, J=6.9 Hz, 6 H, two ester CH$_3$).

Anal. Calcd. for $C_{26}H_{28}N_4O_6$: C, 63.40; H, 5.73; N, 11.38. Found: C, 63.22; H, 5.62; N, 11.63.

(e) Diethyl 2-Methoxy-2-[N-((1-benzyl-5-(benzylamino) imidazole-4-carbonyl)amino]malonate: To a solution of the above diethyl 2-methoxy-2-[N-((1-benzyl-5-(benzalimino) imidazole-4-carbonyl)amino]malonate (2.5 g, 5 mmol) in methanol (100 mL), contained in a Parr hydrogenator bottle, was added 10% Pd-C (250 mg). The mixture was hydrogenated at 40 psi for 45 minutes, the catalyst was filtered over Celite, and the filtrate was evaporated. The residue was purified by rotating disk chromatography on a Chromatotron™ plate, made of silica gel (particle size 15 μm, thickness 4 mm), eluting with chloroform. Appropriate UV-absorbing fractions were pooled and evaporated to afford a syrup, which upon trituration with ether, and standing, gave a white solid. The solid was recrystallized from ether. Yield 2.1 g (85%), mp 96–98 C: $^1$H NMR (DMSO-d$_6$) δ 8.3 (s, 1 H, exchangeable with D$_2$O, NH), 7.4 (s, 1 H, imidazole CH), 7.3–7.0 (m, 10 H, Ph-H), 6.1 (t, J=6.9 Hz, 1 H, exchangeable with D$_2$O, NH), 5.15 (s, 2 H, benzyl CH$_2$), 4.4 (d, J=6.9 Hz, 2 H, benzyl CH$_2$), 4.2 (m, 4 H, two ester CH$_2$), 3.19 (s, 3 H, OMe), 1.16 (t, 6 H, two ester CH$_3$).

Anal. Calcd. for $C_{26}H_{30}N_4O_6$.1H$_2$O: C, 60.96; H, 6.25; N, 10.93. Found: C, 61.27; H, 6.02; N, 11.07.

(f) 3,4-Dibenzyl-4,5,7,8-tetrahydro-6-methoxy-6H-imidazo[4,5-e][1,4]diazepine-5,8-dione: A fresh solution of sodium methoxide, prepared by dissolving cleanly cut sodium metal (300 mg, 13 mg.atom) in anhydrous methanol (100 mL), was charged to a 250-mL round-bottomed flask, equipped with a reflux condenser and a nitrogen gas inlet. The above diethyl 2-methoxy-2-[N-((1-benzyl-5-(benzylamino)imidazole-4-carbonyl)amino]malonate (2.0 g, 4.0 mmol) was added, and the clear solution was heated at reflux for 3 hours under N$_2$ atmosphere. The reaction mixture was cooled in an ice-water bath and neutralized to pH 7 with 1N HCl. Evaporation of the solvents yielded a white mass which was purified by flash chromatography on silica gel (particle size 40–63 μm), eluting with a gradient of chloroform-methanol. Appropriate fractions were pooled and evaporated to obtain a white solid which was recrystallized from methanol-water. Yield 400 mg (26%): $^1$H NMR (DMSO-d$_6$) δ 7.6 (s, 1 H, imidazole CH), 7.46 (d, J=4.5 Hz, 1 H, exchangeable with D$_2$O, NH), 7.33 (m, 10 H, Ph-H), 5.1 (d, 2 H, benzyl CH$_2$), 4.7 (d, J=4.5 Hz, 1 H, CH), 4.2 (s, 2 H, benzyl CH$_2$), 3.42 (s, 3 H, OMe).

(g) 3,4-Dibenzyl-4,5,7,8-tetrahydro-6-hydroxy-6H-imidazo[4,5-e][1,4]diazepine-5,8-dione:

Method A: By Ring-Closure, Followed by Hydrolysis of Diethyl 2-Methoxy-2-[N-((1-benzyl-5-(benzylamino) imidazole-4-carbonyl)amino]malonate: A fresh solution of sodium methoxide, prepared by dissolving cleanly cut sodium metal (300 mg, 13 mg.atom) in anhydrous methanol (100 mL), was charged to a 250-mL round-bottomed flask, equipped with a reflux condenser and a nitrogen gas inlet. The above diethyl 2-methoxy-2-[N-((1-benzyl-5-(benzylamino)imidazole-4-carbonyl)amino]malonate (2.0 g, 4.0 mmol) was added, and the clear solution was heated at reflux for 3 hours under N$_2$ atmosphere. The reaction mixture was cooled in an ice-water bath, and the pH was adjusted to 2–3 with 1N HCl. Upon concentration of the reaction mixture by rotary evaporation, a fluffy, off-white solid separated which was then filtered, washed with water, and dried. Yield 1.0 g (69%), mp 198–200 C: $^1$H NMR (DMSO-d$_6$) δ 12.8 (br s, 1 H, exchangeable with D$_2$O, OH), 7.59 (s, 1 H, imidazole CH), 7.30 (m, 11 H, 10 Ph-H+1 NH, exchangeable with D$_2$O), 5.1 (two d, J=15.9 Hz, 2 H, benzyl CH$_2$), 4.6 (d, J=4.2 Hz, 1 H, CH), 4.1 (two d, J=14.7 Hz, 2 H, benzyl CH$_2$).

Anal. Calcd. for $C_{20}H_{18}N_4O_3$.0.25 H$_2$O: C, 65.51; H, 5.05; N, 15.27. Found: C, 65.36; H, 5.00; N, 15.25.

Method B: By Hydrolysis of 3,4-Dibenzyl-4,5,7,8-tetrahydro-6-methoxy-6H-imidazo[4,5-e][1,4]diazepine-5,8-dione: To a suspension of 60% sodium hydride (25 mg, 0.62 mmol) in dry tetrahydrofuran (30 mL) was added the above 3,4-dibenzyl-4,5,7,8-tetrahydro-6-methoxy-6H-imidazo[4,5-e][1,4]diazepine-5,8-dione (200 mg, 0.53 mmol). The reaction mixture was stirred under N$_2$ atmosphere at room temperature overnight, and the pH was adjusted to 6.5 with 1N HCl. Upon concentration of the reaction mixture by rotary evaporation, a fluffy, off-white solid separated which was filtered, washed with water, and dried. The mp, Rf, and $^1$H NMR of this product were identical to those of 3,4-dibenzyl-4,5,7,8-tetrahydro-6-hydroxy-6H-imidazo[4,5-e][1,4]diazepine-5,8-dione, prepared by Method A above.

(h) 4,5,7,8-Tetrahydro-6-hydroxy-3H, 6H-imidazo[4,5-e] [1,4]diazepine-5,8-dione: A solution of the above 3,4-dibenzyl-4,5,7,8-tetrahydro-6-hydroxy-6H-imidazo[4,5-e] [1,4]diazepine-5,8-dione (500 mg, 1.38 mmol) in glacial acetic acid (20 mL) was transferred to a Parr hydrogenation bottle. To this solution was added 10% (Pd(OH)$_2$ on carbon (100 mg), and the mixture was hydrogenated at 40 psi for 20 hours. The catalyst was removed by filtration through Celite and washed with acetic acid (15 mL). The filtrate, along with washings, was evaporated to dryness under reduced pressure to obtain a colorless residue. The residue was dissolved in H$_2$O and re-precipitated with acetone to obtain a solid. The solid was filtered and dried. $^1$H NMR (DMSO-d$_6$) δ 12.45 (br s, 1 H, exchangeable with D$_2$O, NH), 7.45 (s, 1 H, imidazole CH), 7.28 (s, 1 H, exchangeable with D$_2$O, NH), 6.70 (br s, 1 H, exchangeable with D$_2$O, NH), 4.85 (s, 1 H, CH).

EXAMPLES 7 AND 8

6-Amino-6-methoxycarbonyl-4,5,7,8-tetrahydro-6H-imidazo[4,5-e]-[1,4]diazepine-5,8-dione (Example 7)

[Formula IV, where U,Y,Z,K=C; X,W,J,L=N; $R_1,R_5$=O; $R_3$=NH$_2$; $R_4$=CO$_2$CH$_3$; $R_2,R_6,R_7,R_8$=H; $R_9$=None], and 6-Methoxy-6-methoxycarbonyl-4,5,7,8-tetrahydro-6H-imidazo[4,5-e][1,4]-diazepine-5,8-dione (Example 8)

[Formula IV, where U,Y,Z,K=C; X,W,J,L=N; $R_1,R_5$=O; $R_3$=OCH$_3$; $R_4$=CO$_2$CH$_3$; $R_2,R_6,R_7,R_8$=H; $R_9$=None]

(a) Diethyl 2-[N-(1-Benzyl-5-nitroimidazolyl-4-carbonyl)amino]malonate

A 250-ml three-necked, round-bottomed flask, equipped with a reflux condenser, was charged with 1-benzyl-5-nitroimidazole-4-carboxylic acid (Hosmane, et al., *J. Heterocyclic Chem.* 27:2189 (1990)) (5.0 g, 20 mmole), 1,1'-carbonyldiimidazole (CDI) (4.5 g, 27 mmole), and dry tetrahydrofuran (THF) (150 ml). The mixture was heated at reflux for 4 hours, when a clear solution was formed. The solution was cooled to room temperature, and a freshly prepared solution of diethyl aminomalonate from its hydrochloride salt (5.71 g, 27 mmole) by treatment with triethylamine (4.0 ml, 28.7 mmole) in 100 ml of methylene chloride, was added. The reaction mixture was stirred at room temperature for 1 hour, when a tlc (silica gel, chloroform:methanol, 8:1) showed the formation of a new compound which had a higher Rf than the starting material. The reaction mixture was evaporated to dryness on a rotary evaporator, and the residual gum was suspended in ice-water, and stirred overnight on a magnetic stirrer. A pale yellow solid that separated was filtered, washed with 2×100 ml of water, and dried. The compound was recrystallized from methanol into pale yellow flakes, yield 7.9 g (96%), mp 88; $^1$H nmr (DMSO-d$_6$): δ 9.27 (d, J=7.0 Hz, 1H, exchangeable with deuterium oxide, NH), 8.28 (s, 1H, imidazole CH), 7.38–7.19 (m, 5H, Ph-H), 5.54 (s, 2H, benzyl CH$_2$), 5.23 (d, J=7.5 Hz, 1H, CH), 4.22–4.14 (q, 4H, two ester CH$_2$), 1.21–1.18 (t, 6H, two ester CH$_3$); ms (EI): m/z 331 (M$^+$—CO$_2$Et), 303, 259, 230.

Anal. Calcd. for $C_{18}H_{20}N_4O_7$: C, 53.48; H, 4.98; N, 13.85. Found: C, 53.50; H, 5.03; N, 13.91.

(b) Diethyl 2-Benzylamino-2-[N-(1-benzyl-5-nitroimidazolyl-4-carbonyl)amino]malonate Diethyl 2-[N-(1-benzyl-5-nitroimidazolyl-4-carbonyl) amino]malonate, prepared above, (1.0 g, 2.47 mmol) was added to a stirred solution of NaH (60%) (200 mg, 5.0 mmol) in dry THF at −78° C., followed by the addition of bromine (0.25 mL, 4.3 mmol). It was stirred for 10 minutes, and a solution of benzylamine (0.4 mL, 3.6 mmol) in dry THF (10 mL) was added. The reaction mixture was stirred for an additional hour, and was slowly brought to room temperature. The solvents were evaporated on a rotary evaporator under reduced pressure, and the residue was taken in 50 mL of water. The pH of the solution was adjusted to 7, and it was extracted with chloroform (2×125 mL). The combined organic extracts were successively washed with dilute hydrochloric acid and water, dried over anhydrous magnesium sulfate, filtered, and the filtrate evaporated to dryness. The residue was triturated with ether when an off-white solid separated. The solid was filtered and dried, yield 0.83 g (66%), mp 100–101 C; $^1$H NMR (DMSO-d$_6$): δ 9.09 (s, 1H, exchangeable with deuterium oxide, NH), 8.2 (s, 1H, imidazole CH), 7.40–7.10 (m, 10H, 2×Ph-H), 5.54 (s, 2H, benzyl CH$_2$), 4.14 (q, J=7.0 Hz, 4H, two ester CH$_2$), 3.65 (d, J=6.6 Hz, CH$_2$NH), 3.36 (t, J=6.6 Hz, 1H, exchangeable with deuterium oxide, NH), 1.14 (t, J=7.0 Hz, 6H, two ester CH$_3$).

Anal. Calcd. for $C_{25}H_{27}N_5O_7$: C, 58.92; H, 5.34; N, 13.74. Found: C, 59.02; H, 5.36; N, 13.77.

(c) Diethyl 2-Benzylamino-2-[N-(5-amino-1-benzylimidazolyl-4-carbonyl)amino]malonate A mixture of the above diethyl 2-Benzylamino-2-[N-(1-benzyl-5-nitroimidazolyl-4-carbonyl)amino]malonate (1.0 g, 1.9 mmol) and Pd-C (10%) (100 mg) in absolute methanol (100 mL) was hydrogenated in a Parr hydogenator at 40 psi for 35 minutes. The reaction mixture was filtered through Celite, and the filtrate evaporated to dryness on a rotary evaporator. The residual semi-solid was triturated with ether to obtain a white solid. The solid was filtered and dried, yield 0.74 g (79%), mp 121–123 C; $^1$H NMR (DMSO-d$_6$): δ 7.85 (s, 1H, imidazole CH), 7.37–7.19 (m, 11H, 2×Ph-H+NH), 5.96 (s, 2H, exchangeable with deuterium oxide, NH$_2$), 5.08 (s, 2H, benzyl CH$_2$), 4.10 (q, J=7.0 Hz, 4H, two ester CH$_2$), 3.55 (d, J=6.0 Hz, CH$_2$NH), 3.20 (m, 1H, exchangeable with deuterium oxide, NHCH$_2$), 1.10 (t, J=7.0 Hz, 6H, two ester CH$_3$).

Anal. Calcd. for $C_{25}H_{29}N_5O_5$: C, 62.61; H, 6.09; N, 14.60. Found: C, 62.47; H, 6.12; N, 14.57.

(d) 6-Amino-6-methoxycarbonyl-4,5,7,8-tetrahydro-6H-imidazo[4,5-e][1,4]diazepine-5,8-dione (Example 7) and 6-Methoxy-6-methoxycarbonyl-4,5,7,8-tetrahydro-6H-imidazo[4,5-e][1,4]diazepine-5,8-dione (Example 8)

To a solution of sodium methoxide, freshly prepared by dissolving sodium metal (368 mg, 16 mg.atom) in methanol (25 mL), was added the above diethyl 2-Benzylamino-2-[N-(5-amino-1-benzylimidazolyl-4-carbonyl)amino]malonate (2.0 g, 4.1 mmol), when the color of the reaction mixture changed to dark brown. The mixture was heated to reflux for 2.5 hours. It was cooled, the pH adjusted to 7.5 with 1N HCl, and was evaporated to dryness on a rotary evaporator. The residue was suspended in glacial acetic acid (50 mL), and 20% Pd(OH)$_2$—C (250 mg) was added. The mixture was hydrogenated in a Parr hydrogenator for 18 hours. The reaction mixture was filtered through Celite, and the filtrate evaporated to dryness. The residue was purified by flash chromatography on a silica gel column, eluting first with a mixture of chloroform-methanol (6:1) to collect the faster moving 6-methoxy-6-methoxycarbonyl-4,5,7,8-tetrahydro-6H-imidazo[4,5-e][1,4]-diazepine-5,8-dione (Example 8), recrystallized from MeOH-H$_2$O, mp>280 C; $^1$H NMR (DMSO-d$_6$) δ 12.97 (br s, 1H, exchangeable with D$_2$O, NH), 11.36 (br s, 1 H, exchangeable with deuterium oxide, NH), 8.66 (s, 1H, exchangeable with deuterium oxide, NH), 7.70 (s, 1H, imidazole CH), 3.73 (s, 3H, CO$_2$Me), 3.08 (s, 3H, OMe); MS (EI, 70 eV) m/z 254 (M$^+$).

Further elution of the column with a mixture of chloroform-methanol (4:1) afforded the slower moving 6-amino-6-methoxycarbonyl-4,5,7,8-tetrahydro-6H-imidazo[4,5-e]-[1,4]diazepine-5,8-dione (Example 7), recrystallized from MeOH as white rhombic crystals, mp: sinters at 196° C. and decomposes at 203 C; $^1$H NMR (DMSO-d$_6$) δ 12.93 (br s, 1H, exchangeable with deuterium oxide, NH), 11.13 (br s, 1H, exchangeable with deuterium oxide, NH), 7.83 (s, 1H, exchangeable with deuterium oxide, NH), 7.67 (s, 1H, imidazole CH), 3.4 (s, 3H, CO$_2$Me), 3.0 (s, 2H, exchangeable with deuterium oxide, NH$_2$); MS (EI, 70 eV) m/z 239 (M$^+$).

Anal. Calcd. for $C_8H_9N_5O_4$: C, 40.17; H, 3.78; N, 29.27. Found: C, 40.06; H, 3.74; N, 29.15.

EXAMPLE 9

Inhibition of Adenosine Deaminase by 4,6,8-Triimino-1-β-D-ribofuranosylimidazo[4,5-e][1,3]diazepine (or its tautomer, see Example 4 above)

The inhibition of the hydrolysis of adenosine ($K_m$=2.5× $10^{-5}$ to 3.1×$10^{-5}$) to xanthosine was monitored at 265 nm at 25° C. in a phosphate buffer (pH 7), employing adenosine deaminase (Type IV) from bovine spleen (a suspension in 3.2 M $(NH_4)_2SO_4$, pH 6). The concentration of inhibitor, the title compound, used for the present study ranged from $4.6 \times 10^{-5}$ to $9.2 \times 10^{-5}$ M. The enzyme concentration used for each of the assays was 0.0235 units/mL. As computed by the Lineweaver-Burk plot (refer to any standard Biochemistry text), the title compound was found to be a competitive inhibitor of adenosine deaminase with a $K_i = 3.85 \times 10^{-4}$ to $4 \times 10^{-4}$ M.

EXAMPLES 10 AND 11

Inhibition of Guanase by 6-Amino-6-methoxycarbonyl-4,5,7,8-tetrahydro-6H-imidazo[4,5-e]-[1,4]diazepine-5,8-dione (see Example 7 above) and 6-Methoxy-6-methoxycarbonyl-4,5,7,8-tetrahydro-6H-imidazo[4,5-e][1,4]-diazepine-5,8-dione (see Example 8 above)

The inhibition of the hydrolysis of guanine ($K_m = 6.4 \times 10^{-6}$ to $7.1 \times 10^{-6}$) to xanthine were monitored spectrophotometrically at 248 nm at 21° C. in a Tris buffer (pH 7.6), employing rabbit liver guanase. The concentration of the inhibitor ranged from $4 \times 10^{-5}$M to $8 \times 10^{-5}$M (Example 7), and $4.4 \times 10^{-5}$M to $8.9 \times 10^{-5}$M (Example 8). The concentration of the enzyme used for each assay was 0.0082 units/mL. As computed by the Lineweaver-Burk plot, both of the title compounds were found to be competitive inhibitors of guanase with $K_i$'s equal to $1.9 \times 10^{-4}$M and $5.4 \times 10^{-4}$M, respectively.

EXAMPLE 12

Antiretroviral Activity of 4,5,7,8-Tetrahydro-6H-1-β-D-ribofuranosylimidazo[4,5-e][1,2,4]triazepine [Formula IV, where U,Z,K=C; X,Y,W,J,L=N; $R_1, R_5$=O; $R_2, R_3, R_6, R_7, R_8$=H; $R_4$=None]

(a) Cells and Virus

The continuous murine fibroblast cell line SC-1 was propagated at 37° C. in Eagle's Minimum Essential Medium (MEM), supplemented with 10% fetal bovine serum and 12.5 μg/mL gentamycin. Cas-Br-M murine leukemia virus (MuLV) pools were prepared in SC-1 (Hoffman, et al., *J. Neuroimmunology* 1:272 (1981)). Cell lines derived from infection of SC-1 with Cas-Br-M MuLV chronically produce high titers of infectious ecotropic virus. The virus was stored as aliquots frozen below −70° C.

(b) Viral Infection and the Reverse Transcriptase (RT) Inhibition Assay

SC-1 cells ($10^5$ cells per 60 mm petri dish) were grown in complete medium with 4 μg/mL polybrene overnight. Three hours prior to infection, the media was removed and a medium containing various concentrations of the test compound was added to each of two plates per concentration. As internal controls, a set of duplicate plates were run with no drug or with 1000 units/mL of mouse fibroblast interferon. Cells were incubated at 37° C. for 3 hours to provide for transport and metabolism of the test compound, and then all plates were were infected by the addition of 0.5 mL of the virus at a multiplicity of infection of 0.5 PFU/cell of Cas-Br-M MuLV. At 24 hours post-infection (pi), the medium containing the virus inoculum was removed and replaced with a fresh medium containing the test compound. The cultures were then incubated for 48 hours prior to harvest of the culture fluid. The culture fluids were pooled and clarified by centrifugation at 2000×g. An 8 mL sample was centrifuged at 105,000×g through a 5 mL pad of 20% w/w sucrose, thus pelleting the virus particles and separating them from contaminating cellular debris and the test agent. The pellet was suspended in 80 μL of RT (reverse transcriptase) buffer (50 mM Tris buffer, pH 8.3, containing 1% Triton X-100) affecting a 100-fold concentration of the virus particles. The resulting virus suspension was assayed in an RT assay (J. Bilello, et al., *Proc. Natl. Acad. Sci.* 71:3234 (1974)), using dT.rA as the exogenous primertemplate and tritiated deoxythymidine triphosphate ($^3$H-dTTP) as the label. Briefly, 5–25 μL of the pelleted virions in RT buffer was added to a reaction mixture containing 50 mM Tris (pH 8.3), 20 mM dithiothreitol, 0.6 mM $MnCl_2$, 0.05% NP-40, 5 μg of oligodeoxythymidilic acid ($dT_{10}$), 10 μg of polyriboadenylic acid (poly rA) per mL, and 10 μM $^3$H-dTTP in a total volume of 100 μL. Incorporation of the radiolabeled nucleotide into the trichloroacetic acid (TCA) precipitable product after a 60 minute incubation was determined. Duplicate 40 μL aliquots were transferred to Whatman 3 MM filters, then precipitated with TCA, dried, and the filter-associated radioactive product was counted by liquid scintillation spectrometry. Assay conditions were determined such that the incorporation was directly proportional to the enzyme concentration over a 100 fold concentration range. The data are summarized in the following Table:

TABLE I

| Compound | Concentration | RT Activity |
|---|---|---|
| None (Control) | — | 38,000 |
| Interferon (Reference) | 1000 units/mL | 10,000 |
| The Test Compound | 0.1 μg/mL | 18,600 |
| The Test Compound | 1.0 μg/mL | 9,200 |
| The Test Compound | 10.0 μg/mL | 0 |

What is claimed is:

1. Potentially planar, aromatic, ring-expanded heterocyclic bases, nucleosides and nucleotide compounds having the structure

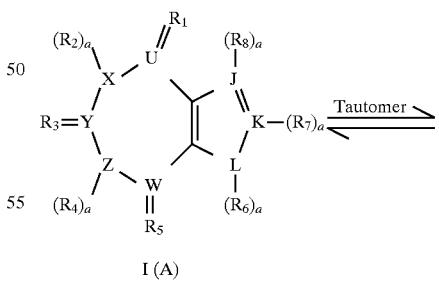

I (A)

-continued

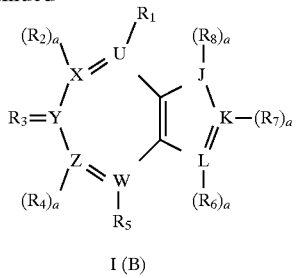

I (B)

Tautomer

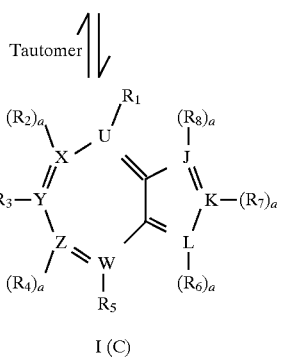

I (C)

wherein:
R$_1$, R$_3$ and R$_5$ are each independently selected from:
  NH, NH$_2$, O, OH, S, and SH;
  NH-alkyl, N-alkyl, O-alkyl and S-alkyl wherein the alkyl group is C$_1$–C$_{20}$;
  NH-aryl, O-aryl and S-aryl wherein the aryl group is a substituted or unsubstituted phenyl or heterocyclic group;
R$_2$, R$_4$, R$_7$, and R$_8$ are independently selected from the group consisting of hydrogen, C$_1$–C$_{20}$ alkyl, substituted phenyl, unsubstituted phenyl, unsubstituted heterocycle, substituted heterocycle, aralkyl wherein the alkyl containing 1 to 6 carbon atoms and the aryl is substituted or unsubstituted;
R$_6$ is selected from the group consisting of
  hydrogen,
  C$_1$–C$_{20}$ alkyl,
  substituted phenyl,
  unsubstituted phenyl,
  unsubstituted heterocycle,
  substituted heterocycle,
  aralkyl wherein the alkyl containing 1 to 6 carbon atoms and the aryl is substituted or unsubstituted:
  a glycosyl group selected from the group consisting of ribosyl, 2'-deoxyribosyl, 2'3'-dideoxyribosyl, 2'3'-dideoxy-2'-fluororibosyl, 2'3'-dideoxy-3'-fluororibosyl, 2'3'-dideoxy-2'3'-fluororibosyl, 2'3'-dideoxy-3'-azidoribosyl and mono-, di-, and triphosphate derivatives thereof;
  —(CH$_2$)$_{m+n+1}$—R'
  —(CH$_2$)$_m$—O—(CH$_2$)$_n$—O—R';
  —(CH$_2$)$_{m+1}$—O—R';
  —(CH$_2$)$_m$—O—(CH$_2$)$_n$—R';
wherein R' is selected from the group consisting of: hydrogen, H$_2$PO$_3$, H$_3$P$_2$O$_6$, H$_4$P$_3$O$_9$, and alkali metal or alkaline earth metal salts thereof;
m is zero to 20, n is zero to 20, and a is zero or one;
U, X, Y, Z, W, J, K, and L are selected from the group consisting of C and N;
and all chiral forms and stereoisomers of said compounds.

2. A compound according to claim 1, wherein U, X, Y, Z, W, J, K and L are selected from the group consisting of carbon (C) and nitrogen (N).

3. A compound according to claim 2, wherein U, Y, W and K are C and X, Z, J and L are N.

4. A compound having the formula I(B) according to claim 3, which is 4,8-diamino-6-imino-1H-imidazo[4,5-e][1,3]diazepine wherein R, and R$_5$ are NH$_2$, R$_3$ is NH, R$_7$ and R$_8$ are H, and a for R$_2$, R$_4$ and R$_6$ is zero.

5. A compound having the formula I(B) according to claim 3, which is 4,8-diamino-1-benzyl-6-iminoimidazo[4,5-e][1,3]diazepine, wherein R$_1$ and R$_5$ are NH$_2$, R$_3$ is NH, R$_7$ is H, R$_8$ is benzyl (CH$_2$Ph) and a for R$_2$, R$_4$ and R$_6$ is zero.

6. A compound having formula I(A) according to claim 2, which is 6-imino-1H-imidazo[4,5-e][1,3]diazepine-4,8-dione, wherein R$_1$ and R$_5$ are O, R$_3$ is NH; R$_2$, R$_4$, R$_6$ and R$_7$ are H, and a is zero for R$_8$.

7. A compound according to claim 3, having formula I(A), which is 4,6,8-triimino-1-β-D-ribofuranosylimidazo[4,5-e][1,3]diazepine, wherein R$_1$, R$_3$ and R$_5$ are NH, R$_2$, R$_4$ and R$_7$ are H, R$_6$ is 1-β-D-ribofuranosyl, and a for R$_8$ is zero.

8. Compounds comprising non-planar, non-aromatic, ring-expanded ("fat") heterocyclic bases, nucleosides or nucleotides having the formula II

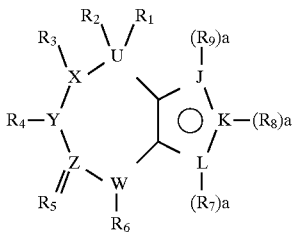

Formula II wherein:
R$_1$ and R$_2$ are each independently selected from H, OR$_3$, SR$_3$, NHR$_3$, CO$_2$R$_3$, CONHR$_3$, CONHNHR$_3$, CH$_2$OR$_3$, CH$_2$NHR$_3$, and CH$_2$R$_3$;
R$_3$, R$_4$ and R$_6$ are each independently selected from:
  hydrogen, a C$_1$–C$_{20}$ alkyl group, an aryl group which is a substituted or unsubstituted phenyl or heterocyclic group, and an aralkyl group wherein the aryl and alkyl portions of the group have the meanings given above;
R$_5$ is selected from the group consisting of O, S and NH; and
R$_7$, R$_8$ and R$_9$ each are independently selected from:
  hydrogen, a C$_1$–C$_{20}$ alkyl group, an aryl group which is a substituted or unsubstituted phenyl or heterocyclic group, and an aralkyl group wherein the aryl and alkyl portions of the groups have the meanings given above;
  a glycosyl group wherein said glycosyl group is selected from the group consisting of ribosyl, 2'-deoxyribosyl, 2'3'-dideoxy-3'-azidoribosyl, 2'3'-dideoxy-2'-fluororiboxyl, 2',3'-dideoxy-3'-fluororibosyl, 2',3'-dideoxy-2',3'-difluororiboxyl, and mono-, di- and triphosphate derivatives thereof; and
  (CH$_2$)$_m$—XR'—(CH$_2$)$_n$—YR' wherein R' is selected from the group consisting of:
  H, H$_2$, H$_2$PO$_3$, H$_3$P$_2$O$_6$, H$_4$P$_3$O$_9$, and alkali metal or alkaline earth metal salts thereof;
  m is zero to 20, n is zero to 20, and a is zero or one;
  U, X, Y, Z, W, J, K, and L are selected from the group consisting of C, N, O, P, and S;

and all chiral form and stereoisomers of said compounds.

9. Compounds according to claim 8, wherein U, X, Y, Z, W, J, K and L are selected from C and N.

10. Compounds according to claim 9, wherein U, X, Z and K are C and Y, W, J and L are N.

11. Compound according to claim 10, which is 4,5,6,7-tetrahydro-8-hydroxy-8H-1-β-D-ribofuranosyl[4,5-d][1,3] diazepine-5-one wherein $R_1$ is OH, $R_2$, $R_4$, $R_6$ and $R_8$ are H, $R_5$ is O, $R_3$ is $H_2$, $R_9$ is 1-β-D-ribofuranosyl, and a for $R_7$ is zero.

12. Compounds comprising non-planar, non-aromatic, ring-expanded ("fat") heterocyclic bases, nucleosides or nucleotides having the following formulas III and IV

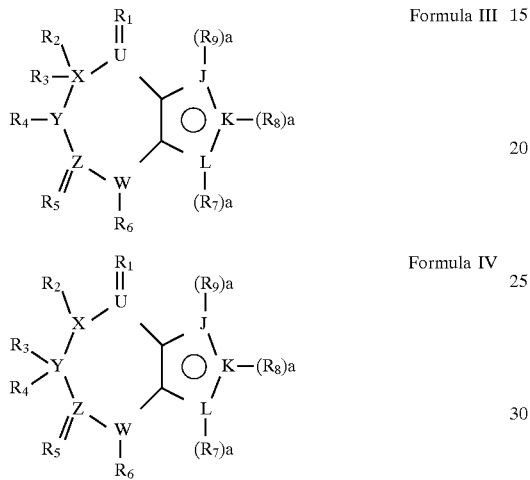

wherein:
$R_1$ and $R_5$ are each independently selected from O, S, and NH;

$R_3$ and $R_4$ are each independently selected from H, $OR_2$, $SR_2$, $NHR_2$, $CO_2R_2$, $CONHR_2$, $CONHNHR_2$, $CH_2OR_2$, $CH_2NHR_2$, and $CH_2R_2$;

$R_2$, $R_4$ and $R_6$ are each independently selected from: hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

$R_7$, $R_8$, and $R_9$ are each independently selected from: hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;

a glycosyl group wherein said glycosyl group is selected from the group consisting of ribosyl, 2'-deoxyribosyl, 2'3'-dideoxy-3'-azidoribosyl, 2',3'-dideoxy-2'-fluororibosyl, 2',3'-dideoxy-3'-fluororibosyl, 2',3'-dideoxy-2'3'-difluororibosyl, and mono-, di-, and triphosphate derivatives thereof;

$(CH_2)_m$—XR'—$(CH_2)_n$—YR' wherein R' is selected from:
hydrogen, $H_2PO_3$, $H_3P_2O_6$, $H_4P_3O_9$, and alkali metal or alkaline earth metal salts thereof;
m is zero to 20, n is zero to 20, and a is zero or one;
U, X, Y, Z, W, J, K, and L are selected from the group consisting of C, N, O, P, and S;
and all chiral forms and stereoisomers of said compounds.

13. Compounds according to claim 12 having formula IV, wherein U, X, Y, Z, W, J, K and L are selected from C and N.

14. Compounds according to claim 13, wherein U, Y, Z and K are C and X, W, J and L are N.

15. A compound according to claim 14, which is 4,5,7,8-tetrahydro-6-hydroxy-3H,6H-imidazo[4,5-e][1,4] diazepine-5,8-dione, wherein $R_1$ and $R_5$ are O, $R_3$ is OH, $R_2$, $R_4$, $R_6$, $R_7$ and $R_8$ are H, and a for $R_9$ is zero.

16. A pharmaceutical composition comprising at least one of said compounds of claims 1, 8, or 12 and a pharmaceutically acceptable carrier.

* * * * *